(12) United States Patent
Katsuda et al.

(10) Patent No.: US 9,339,524 B2
(45) Date of Patent: May 17, 2016

(54) DRUG INHIBITING THE PROGRESSION OF ATHEROSCLEROSIS, PREVENTIVE DRUG, BLOOD CHOLESTEROL-LOWERING DRUG, FUNCTIONAL FOOD, AND SPECIFIC HEALTH FOOD

(75) Inventors: Shogo Katsuda, Ishikawa (JP); Lihua Tang, Ishikawa (JP); Yasuo Sakai, Miyagi (JP)

(73) Assignees: JELLICE CO., LTD., Miyagi (JP); KANAZAWA MEDICAL UNIVERSITY, Ishikawa (JP)

( * ) Notice: Subject to any disclaimer, the term of this patent is extended or adjusted under 35 U.S.C. 154(b) by 228 days.

(21) Appl. No.: 13/255,651

(22) PCT Filed: Mar. 11, 2010

(86) PCT No.: PCT/JP2010/001734
§ 371 (c)(1),
(2), (4) Date: Dec. 15, 2011

(87) PCT Pub. No.: WO2010/103837
PCT Pub. Date: Sep. 16, 2010

(65) Prior Publication Data
US 2013/0123167 A1 May 16, 2013

(30) Foreign Application Priority Data
Mar. 11, 2009 (JP) .................... 2009-057444

(51) Int. Cl.
*A61K 38/06* (2006.01)
*A23L 1/305* (2006.01)
*C07K 5/083* (2006.01)

(52) U.S. Cl.
CPC ............... *A61K 38/06* (2013.01); *A23L 1/3053* (2013.01); *C07K 5/0806* (2013.01); *A23V 2002/00* (2013.01)

(58) Field of Classification Search
CPC ................ A23V 2002/00; A23V 2200/326; A23V 2200/3262; A23V 2250/0604; A23V 2250/0606; A23V 2250/0622; A23V 2250/06; A23V 2250/0626; A23V 2250/0628; A23V 2250/063; A23V 2250/0632; A23V 2250/064; A23V 2250/0648; A23V 2250/55; A23L 1/3053; A61K 38/06; C07K 5/0806
See application file for complete search history.

(56) References Cited

U.S. PATENT DOCUMENTS

| | | | |
|---|---|---|---|
| 5,643,892 A | 7/1997 | Striker et al. | |
| 6,956,120 B2 | 10/2005 | Ikewaki et al. | |
| 7,601,807 B2 | 10/2009 | Kanayama et al. | |
| 7,855,273 B2 | 12/2010 | Kanayama et al. | |
| 7,871,797 B2 | 1/2011 | Kanayama et al. | |
| 2001/0005720 A1 | 6/2001 | Striker et al. | |
| 2002/0183384 A1 | 12/2002 | Cornicelli et al. | |

FOREIGN PATENT DOCUMENTS

| | | | | |
|---|---|---|---|---|
| JP | 57-145846 | 9/1982 | | |
| JP | 11(1999)-49802 | 2/1999 | | |
| JP | 2000-102381 | 4/2000 | | |
| JP | 2001-031586 | 2/2001 | | |
| JP | 2002-204687 | 7/2002 | | |
| JP | 2002-275062 | 9/2002 | | |
| JP | 2003-048889 | 2/2003 | | |
| JP | 2003-137807 | 5/2003 | | |
| JP | 2003284551 A | * 10/2003 | ............. A61K 38/00 | |
| JP | 2004-035475 | 2/2004 | | |
| JP | 2004-350513 | 12/2004 | | |
| JP | 2005029488 A | * 2/2005 | ............. A61K 38/00 | |
| JP | 2005-263758 | 9/2005 | | |
| JP | 2005-281186 | 10/2005 | | |
| JP | 2007-182448 | 7/2007 | | |
| JP | 2007-231225 | 9/2007 | | |
| JP | 2008-024611 | 2/2008 | | |
| WO | WO 2008/059927 | 5/2008 | | |
| WO | WO 2009035169 A1 | * 3/2009 | ............... C07K 5/00 | |

OTHER PUBLICATIONS

G.S. Getz, HDL apoplipoprotein-related peptides in the treatment of atherosclerosis and other inflammatory disorders, Curr Pharm Des. 2010:16(28):3173-3184.*
JP 2003-137807 A, English Translation of Specification provided, May 14, 2003.*
JP2005029488, English Translation of the Specification, Feb. 2005.*
JP2003284551, English Translation of the Specification, Oct. 2003.*
William Hollander, Hypertension, Antihypertensive Drugs and Atherosclerosis, Circulation, 1973; 48:1112-1127.*
English Translation of WO2009035169 A1, Mar. 2009.*
Se-Kwon Kim, Angiotensin I Converting Enzyme Inhibitory Peptides Purified from Bovine Skin Gelatin Hydrolysate, J. Agric. Food Chem. 2001, 49, 2992-2997.*
Giuseppe Coppola, Peripheral Artery disease: potential role of ACE-inhibitory therapy, Vascular Health and Risk Management, 2008:4(6), pp. 1179-1187.*

(Continued)

*Primary Examiner* — James H Alstrum Acevedo
*Assistant Examiner* — Erinne Dabkowski
(74) *Attorney, Agent, or Firm* — Ditthaving & Steiner, P.C.

(57) ABSTRACT

Disclosed are a novel therapeutic agent and a novel prophylactic agent for atherosclerosis, a blood cholesterol level-lowering agent, and a functional food or a food for specified health uses effective for the inhibition and/or prevention of aging of blood vessels or inflammation in blood vessels. Specifically disclosed are an inhibitor of the progression of atherosclerosis, a prophylactic agent for atherosclerosis, a blood cholesterol level-lowering agent, and a functional food and a food for specified health uses both effective for the inhibition and/or prevention of aging of blood vessels or inflammation in blood vessels, each of which comprises, as an active ingredient, a hydrolysis product of a collagen comprising at least one collagen tripeptide Gly-X-Y [wherein Gly-X-Y represents an amino acid sequence; and X and Y independently represent an amino acid residue other than Gly].

8 Claims, 15 Drawing Sheets

(56) References Cited

OTHER PUBLICATIONS

Min-Suk Ma, Purification and identification of angiotensin I-converting enzyme inhibitory peptide from buckwheat (*Fagopyrum esculentum* Moench), Food Chemistry 96 (2006) 36-42.*

Rumiko Yamato et al., "Favorable Effects of Collagen Tripeptide (HACP) on Healing of Bone Tissue and Achilles Tendons", FFI Journal, vol. 210, No. 9, 2005, pp. 854-858.

Stehbens,."Atherosclerosis and degenerative diseases of blood vessels", Vascular Pathology, 1995, pp. 175-269, Chapman and Hall, London.

Katsuda, "From the standpoint of human pathology, Arteriosclerosis", 2001, vol. 28, No. 3, pp. 69-73.

Ross, "The pathogenesis of atherosclerosis: a perspective for the 1990s", Nature 1993; vol. 362; pp. 801-809.

Watanabe et al., "Atherosclerosis, Sogo Rinsho", 1984, vol. 33, No. 3, pp. 647-655.

Humbert et al., "Intranuclear co-location of newly replicated DNA and PCNA by simultaneous immunofluorescent labelling and confocal microscopy in MCF-7 cells", J Cell Sci, 1992, 103, pp. 97-103.

Koyama et al., "Fibrillar collagen inhibits arterial smooth muscle proliferation through regulation of Cdk2 inhibitors", Cell, 1996, vol. 87, pp. 1069-1078.

Ichii et al., "Fibrillar Collagen Specifically Regulates Human Vascular Smooth Muscle Cell Genes Involved in Cellular Responses and the Pericellular Matrix Environment", Circulation Research, 2001, pp. 460-467.

Ross, "Atherosclerosis—An inflammatory disease", The New England Journal of Medicane, 1999, vol. 340, No. 2, pp. 115-126.

Libby, "Molecular bases of the acute coronary syndromeS", Circulation, 1995, vol. 91, No. 11, pp. 2844-2850.

Aikawa, "The stabilization of arteriosclerotic change by lipid-reducing treatments, Experimental Medicine", 2000, 18, pp. 145-151.

International Search Report for corresponding International Application No. PCT/JP2010/001734, Jun. 15, 2010.

International Preliminary Report on Patentability with Written Opinion of the International Searching Authority for corresponding International Application No. PCT/JP2010/001734, Mar. 15, 2011.

Extended European Search Report for corresponding EP Application No. 10750593.5-2107, Oct. 30, 2012.

Office Action for corresponding Japanese Application No. 2011-503722, mailed Apr. 8, 2014, 5 pages. (English Summary of Office Action included).

* cited by examiner

A

B

*, P<0.05 vs control group

*, P<0.01 vs control group

Analysis by staining with azan

*, P<0.05 vs control group (The values show Mean SD (n=5) for CTP group or control group)

A

RAM11

B

HHF35

Analysis by staining with RAM11, HHF35 (1)

**, P<0.01 vs control group
*, P<0.05 vs control group

Analysis by staining with RAM11, HHF35 (2)

*, P<0.05 vs control group

** P<0.01 vs 0 ug/ml

** P<0.01 vs 0 ug/ml

DA
** P<0.01 vs 0 ug/ml

LDA
** P<0.01 vs 0 ug/ml

DRUG INHIBITING THE PROGRESSION OF ATHEROSCLEROSIS, PREVENTIVE DRUG, BLOOD CHOLESTEROL-LOWERING DRUG, FUNCTIONAL FOOD, AND SPECIFIC HEALTH FOOD

CROSS-REFERENCE TO RELATED PATENT APPLICATIONS

The present application claims priority under Japanese Patent Application 2009-57444, filed on Mar. 11, 2009, the entire contents of which are hereby incorporated by reference.

TECHNICAL FIELD

The present invention relates to a drug inhibiting the progression of atherosclerosis, a preventive drug, and a blood cholesterol-lowering drug. More particularly, the present invention relates to a drug inhibiting the progression of atherosclerosis, a preventive drug, and a blood cholesterol-lowering drug containing active ingredients in the form of the hydrolysis products of collagen containing collagen tripeptides. The present invention further relates to a functional food and to a specific health food containing active ingredients in the form of the hydrolysis products of a collagen containing collagen tripeptides that reduces and prevents vascular aging and inflammation.

BACKGROUND ART

Patent applications have been filed for various compounds that target a number of factors relating to causative mechanisms in the prevention of atherosclerosis (Patent References 1 to 5).

In addition to novel compounds, numerous methods of preventing/reducing atherosclerosis by consuming natural substances have been proposed, such as the method of orally administering medicinal activated charcoal (Patent Reference 6) and the method of consuming cultures of black yeast as a health supplement (Patent Reference 7).

The collagens are a diverse but related group of molecules. They have various different biochemical and physical properties. However, they share the same triple helix domains comprised of three polypeptide strands referred to as alpha chains. Each alpha chain contains a high ratio of glycine. Glycine is present in a three amino acid sequence that regularly repeats, which can be denoted as Gly-X-Y. Proline is an amino acid that is present relatively frequently at X, and hydroxyproline is an amino acid that is present relatively frequently at Y. In this conformation, glycine and peptide bonds are buried within the molecule, imparting collagen with high resistance to protein degradation.

Fractions of highly purified nonantigenic and low-allergenic tripeptides containing Gly-X-Y sequences, known as collagen tripeptides (CTP), can be prepared by using bacterial collagenase (Patent References 8 and 9) that cleaves the peptide bonds of type I collagen at the amino terminus of glycine (Patent Reference 10).

Studies conducted in recent years suggest that CTP can regulate the production of collagen by upregulating the secretion activity of fibroblasts, and exhibits bioactivity in many organs such as the skin, bone, and cartilage (Nonpatent Reference 1). It also exhibits the effect of reducing pain in joints (Nonpatent Reference 2).

Wound healing agents; ameliorating, healing-promoting, and preventive agents for tendon and ligament injuries and the like; tendon and ligament ameliorating and fortifying agents; ameliorating, healing-promoting, and preventive agents for flexor tendon and ligament injuries and tears in racehorses; ameliorating and fortifying agents for flexor tendons and ligaments in racehorses; functional foods and pharmaceuticals containing such wound healing agents; and the like containing CTP as an active ingredient have been proposed (Patent Reference 11).

Patent References

[Patent Reference 1] JP-A-H11 (1999)-49802
[Patent Reference 2] JP-A-2003-48889
[Patent Reference 3] JP-A-2004-35475
[Patent Reference 4] JP-A-2002-275062
[Patent Reference 5] JP-A-2005-263758
[Patent Reference 6] JP-A-2007-182448
[Patent Reference 7] JP-A-2002-204687
[Patent Reference 8] JP-A-2000-102381
[Patent Reference 9] JP-A-2004-350513
[Patent Reference 10] JP-A-2007-231225
[Patent Reference 11] JP-A-2005-281186
[Patent Reference 12] JP-A-2001-31586

Nonpatent References

[Nonpatent Reference 1] The effects of the collagen tripeptide HACP on bone and tendon, *FFI Journal*, Vol. 210 (September issue), 854-858 (2005) (in Japanese).
[Nonpatent Reference 2] The 12th Meeting of the Japanese Osteoarthritis Research Society/K. Maruyama et al. (in Japanese)
[Nonpatent Reference 3] Stehbens W E: *Atherosclerosis and degenerative diseases of blood vessels*. In. *Vascular Pathology*. ed by Stehbens and Lie J T, pp 175-269, Chapman and Hall Medical, London, 1995
[Nonpatent Reference 4] Shogo Katsuda: From the standpoint of human pathology, *Arteriosclerosis*, 2001, Vol. 28, No. 3, 69-73 (in Japanese).
[Nonpatent Reference 5] Ross R: *The pathogenesis of atherosclerosis: a perspective for the 1990s*. Nature 1993; 362:801-809.
[Nonpatent Reference 6] Teruo Watanabe et al., Atherosclerosis, Sogo Rinsho, 1984, 33: 647-655 (in Japanese).

The disclosures of Patent References 1 to 12 and Nonpatent References 1 to 6 are expressly incorporated herein by reference in their entirety.

SUMMARY OF THE INVENTION

Problem to be Solved by the Invention

Human atherosclerosis occurs soon after birth, and gradually and quietly progresses. After about age 50, various clinical symptoms appear and pathological change continues (Nonpatent Reference 3). In pathological investigation, severe atherosclerosis is sometimes found even among the young, and almost no pathological change is sometimes found in the arteries of the elderly. This is because atherosclerosis is a phenomenon that advances gradually over an extended period, with various factors such as living habits and social factors greatly affecting the degree of pathological change (Nonpatent Reference 4). As stated by Thomas Sydenham ("A man, is as old as his arteries"), atherosclerosis is profoundly related to humans growing old and aging. The arteries are comprised of the three layers of the intima, the media, and the adventitia. As an artery grows old and ages, pathologically, there is an increase in smooth muscle cells and diffuse thickening due to the accumulation of interstitial components including collagen fiber in the intima. The media undergoes degeneration and rupturing of elastic fiber, and fibrosis. Atherosclerosis and vascular aging are mutually and intimately related.

In atherosclerosis, which has become a disease of increasing importance in recent years, an inflammatory reaction takes place in the intima of the arteries. Smooth muscle cells, macrophages, and T lymphocytes infiltrate and proliferate. Lipids (primarily cholesterol and cholesterol esters) accumulate on the interior and exterior of the cells of the intima, causing the intima to thicken (plaque formation). Based on this onset mechanism, atherosclerosis has been understood in recent years to be a type of inflammation of the blood vessels. When large amounts of lipids deposit outside cells, the plaque weakens, ruptures, and forms blood clots. This is accompanied by acute myocardial infarction and cerebral infarction. In the present specification, the loci of atherosclerosis will sometimes be denoted simply as "plaque."

Smooth muscle cells (SMC) are the principal cellular component of the arterial media. They impart a normal structure to an artery and contract and expand in response to stimuli. They have important physical functions such as synthesizing components of the extracellular matrix such as collagen and elastin, and secreting numerous cytokines. Further, the migration of medial smooth muscle cells into the intima and their proliferation there is an important phenomenon that is the basis of the initiation and progression of atherosclerosis (Nonpatent Document 5). Thus, SMCs are a major and decisive factor in the structure and function of the arteries. Abnormalities in their function and distribution contribute profoundly to the pathological processes of atherosclerosis and other pathological change in the arteries.

Hyperlipidemia treatments (statins and fibrates), for example, are employed to treat atherosclerosis. Hyperlipidemia treatments are drugs with the primary goal of reducing the lipids in the blood, and do not inhibit the progression of atherosclerosis in which SMCs play a direct role. There is no drug at present that directly targets the effects of collagen-producing cells in the form of SMCs.

Chemical substances, particularly synthesized products, present a risk of side effects in the human body. They require considerable investigation into controlling their effects and properties all the way through to the actual product stage, which takes time. Natural substances can often be consumed orally. However, they have various effects and efficacy, and may present a problem in the form of the difficulty of quality control. Further, as of today, no existing product decisively prevents or cures atherosclerosis.

The initial pathological changes of atherosclerosis are observed in the arteries of almost all children when they reach an age somewhere between 2 and 15. The increase in pathological change becomes marked with the attainment of adolescence. About 30% of the arterial surfaces undergo pathological change by the age of 20 to 30 (Nonpatent Reference 6). Accordingly, even for a healthy person who has not yet become aware of, or exhibited the onset of, atherosclerosis, there is a need for functional foods and specific health foods that have the effect of inhibiting or preventing the effects of aging and inflammation of the blood vessels and can be anticipated to have the effect of inhibiting or preventing the progression of atherosclerosis.

Accordingly, the object of the present invention is to provide a new atherosclerosis treatment or preventive drug containing an active ingredient that has some effect on the SMCs that play important roles in the development of atherosclerosis. A further object of the present invention is to provide a blood cholesterol-lowering drug that has the effect of lowering blood cholesterol related to atherosclerosis. An addition object of the present invention is to provide a functional food and a specific health food that is effective to inhibition and prevention of the progression of atherosclerosis.

It was not known that the above CTP had any effect on SMCs. Accordingly, the present inventors employed aortic smooth muscle cells (AoSMCs) to examine whether or not CTP had any effect on the migration and proliferation of smooth muscle cells. As a result, they discovered that migration and proliferation were inhibited in a culture of smooth muscle cells to which CTP had been added. Further, when familial hypercholesterolemic model rabbits were employed in an oral administration experiment, a clear result that exceeded initial expectations was achieved in that it was possible to inhibit the initiation and progression of atherosclerosis itself. The present invention was devised based on this knowledge.

Means of Solving the Problem

The present invention, which solves the above problems, is as follows:

[1]
A drug that inhibits or prevents the progression of atherosclerosis, comprising an active ingredient in the form of the hydrolysis product of a collagen containing at least one collagen tripeptide Gly-X-Y (where Gly-X-Y denotes an amino acid sequence in which X and Y denote amino acid residues other than Gly).

[2]
The drug that inhibits or prevents the progression of atherosclerosis according to [1], wherein the hydrolysis product of a collagen comprises 25 to 100 mass % of the collagen tripeptide Gly-X-Y.

[3]
The drug that inhibits or prevents the progression of atherosclerosis according to [1] or [2], wherein the collagen tripeptide Gly-X-Y is at least one peptide selected from the group consisting of Gly-Ala-Asp, Gly-Ala-Lys, Gly-Ala-Val, Gly-Pro-Gln, Gly-Pro-Met, Gly-Pro-Ile, Gly-Pro-Thr, Gly-Pro-Val, Gly-Ser-Hyp, Gly-Lys-Asp, Gly-Ala-Ala, Gly-Pro-Hyl, Gly-Leu-Hyp, Gly-Ala-Arg, Gly-Ala-Ser, Gly-Ala-Hyp, Gly-Gln-Glu, Gly-Glu-Gln, Gly-Pro-Ser, Gly-Pro-Lys, Gly-Pro-Ala, Gly-Pro-Pro, Gly-Pro-Arg and Gly-Pro-Hyp.

[4]
The drug that inhibits or prevents the progression of atherosclerosis according to any one of [1] to [3], wherein the hydrolysis product of a collagen further comprises Gly-X or X-Y that is the degradation product of a collagen tripeptide Gly-X-Y.

[5]
A blood cholesterol-lowering drug comprising an active ingredient in the form of the hydrolysis product of a collagen containing at least one collagen tripeptide Gly-X-Y (where Gly-X-Y denotes an amino acid sequence in which X and Y denote amino acid residues other than Gly).

[6]
The blood cholesterol-lowering drug according to [5], wherein the hydrolysis product of a collagen comprises 25 to 100 mass % of the collagen tripeptide Gly-X-Y.

[7]
The blood cholesterol-lowering drug according to [5] or [6], wherein the collagen tripeptide Gly-X-Y is at least one peptide selected from the group consisting of Gly-Ala-Asp, Gly-Ala-Lys, Gly-Ala-Val, Gly-Pro-Gln, Gly-Pro-Met, Gly-Pro- Ile, Gly-Pro-Thr, Gly-Pro-Val, Gly-Ser-Hyp, Gly-Lys-Asp, Gly-Ala-Ala, Gly-Pro-Hyl, Gly-Leu-Hyp, Gly-Ala-Arg, Gly-Ala-Ser, Gly-Ala-Hyp, Gly-Gln-Glu, Gly-Glu-Gln, Gly-Pro-Ser, Gly-Pro-Lys, Gly-Pro-Ala, Gly-Pro-Pro, Gly-Pro-Arg and Gly-Pro-Hyp.

[8]
The blood cholesterol-lowering drug according to any one of [5] to [7], wherein the hydrolysis product of a collagen further comprises Gly-X or X-Y that is the degradation product of a collagen tripeptide Gly-X-Y.

[9]
A functional food or a specific health food that is effective to inhibition and/or prevention of the aging and inflammation of blood vessels, comprising an active ingredient in the form of the hydrolysis product of a collagen containing at least one collagen tripeptide Gly-X-Y (where Gly-X-Y denotes an amino acid sequence in which X and Y denote amino acid residues other than Gly).

[10]
The functional food or specific health food according to [9], wherein the hydrolysis product of a collagen comprises 15 to 100 mass % of the collagen tripeptide Gly-X-Y.

[11]
The functional food or specific health food according to [9] or [10], wherein the collagen tripeptide Gly-X-Y is at least one peptide selected from the group consisting of Gly-Ala-Asp, Gly-Ala-Lys, Gly-Ala-Val, Gly-Pro-Gln, Gly-Pro-Met, Gly-Pro-Ile, Gly-Pro-Thr, Gly-Pro-Val, Gly-Ser-Hyp, Gly-Lys-Asp, Gly-Ala-Ala, Gly-Pro-Hyl, Gly-Leu-Hyp, Gly-Ala-Arg, Gly-Ala-Ser, Gly-Ala-Hyp, Gly-Gln-Glu, Gly-Glu-Gln, Gly-Pro-Ser, Gly-Pro-Lys, Gly-Pro-Ala, Gly-Pro-Pro, Gly-Pro-Arg and Gly-Pro-Hyp.

[12]
The functional food or specific health food according to any one of [9] to [11], wherein the hydrolysis product of a collagen further comprises Gly-X or X-Y that is the degradation product of a collagen tripeptide Gly-X-Y.

[13]
A method of inhibiting the progression of, or preventing, atherosclerosis, comprising administering to a patient an effective quantity of the hydrolysis product of a collagen containing at least one collagen tripeptide Gly-X-Y (where Gly-X-Y denotes an amino acid sequence in which X and Y denote amino acid residues other than Gly).

[14]
The method of inhibiting the progression of, or preventing, atherosclerosis of [13], wherein the hydrolysis product of a collagen comprises 25 to 100 mass % of the collagen tripeptide Gly-X-Y.

[15]
The method of inhibiting the progression of, or preventing, atherosclerosis of [13] or [14], wherein the collagen tripeptide Gly-X-Y is at least one peptide selected from the group consisting of Gly-Ala-Asp, Gly-Ala-Lys, Gly-Ala-Val, Gly-Pro-Gln, Gly-Pro-Met, Gly-Pro-Ile, Gly-Pro-Thr, Gly-Pro-Val, Gly-Ser-Hyp, Gly-Lys-Asp, Gly-Ala-Ala, Gly-Pro-Hyl, Gly-Leu-Hyp, Gly-Ala-Arg, Gly-Ala-Ser, Gly-Ala-Hyp, Gly-Gln-Glu, Gly-Glu-Gln, Gly-Pro-Ser, Gly-Pro-Lys, Gly-Pro-Ala, Gly-Pro-Pro, Gly-Pro-Arg and Gly-Pro-Hyp.

[16]
The method of inhibiting the progression of, or preventing, atherosclerosis of any one of [13] to [15], wherein the hydrolysis product of a collagen further comprises Gly-X or X-Y that is the degradation product of a collagen tripeptide Gly-X-Y.

[17]
A collagen decomposition product for use in inhibiting the progression of, or preventing, atherosclerosis, containing at least one collagen tripeptide Gly-X-Y (where Gly-X-Y denotes an amino acid sequence in which X and Y denote amino acid residues other than Gly).

[18]
The hydrolysis product according to [17], wherein the hydrolysis product of a collagen comprises 25 to 100 mass % of the collagen tripeptide Gly-X-Y.

[19]
The hydrolysis product according to [17] or [18], wherein the collagen tripeptide Gly-X-Y is at least one peptide selected from the group consisting of Gly-Ala-Asp, Gly-Ala-Lys, Gly-Ala-Val, Gly-Pro-Gln, Gly-Pro-Met, Gly-Pro-Ile, Gly-Pro-Thr, Gly-Pro-Val, Gly-Ser-Hyp, Gly-Lys-Asp, Gly-Ala-Ala, Gly-Pro-Hyl, Gly-Leu-Hyp, Gly-Ala-Arg, Gly-Ala-Ser, Gly-Ala-Hyp, Gly-Gln-Glu, Gly-Glu-Gln, Gly-Pro-Ser, Gly-Pro-Lys, Gly-Pro-Ala, Gly-Pro-Pro, Gly-Pro-Arg and Gly-Pro-Hyp.

[20]
The hydrolysis product of any one of [17] to [19], wherein the hydrolysis product of a collagen further comprises Gly-X or X-Y that is the degradation product of a collagen tripeptide Gly-X-Y.

[21]
A method of lowering blood cholesterol, comprising administering to a patient an effective quantity of the hydrolysis product of a collagen containing at least one collagen tripeptide Gly-X-Y (where Gly-X-Y denotes an amino acid sequence in which X and Y denote amino acid residues other than Gly).

[22]
The method of lowering blood cholesterol of [21], wherein the hydrolysis product of a collagen comprises 25 to 100 mass % of the collagen tripeptide Gly-X-Y.

[23]
The method of lowering blood cholesterol of [21] or [22], wherein the collagen tripeptide Gly-X-Y is at least one peptide selected from the group consisting of Gly-Ala-Asp, Gly-Ala-Lys, Gly-Ala-Val, Gly-Pro-Gln, Gly-Pro-Met, Gly-Pro-Ile, Gly-Pro-Thr, Gly-Pro-Val, Gly-Ser-Hyp, Gly-Lys-Asp, Gly-Ala-Ala, Gly-Pro-Hyl, Gly-Leu-Hyp, Gly-Ala-Arg, Gly-Ala-Ser, Gly-Ala-Hyp, Gly-Gln-Glu, Gly-Glu-Gln, Gly-Pro-Ser, Gly-Pro-Lys, Gly-Pro-Ala, Gly-Pro-Pro, Gly-Pro-Arg and Gly-Pro-Hyp.

[24]
The method of lowering blood cholesterol of any one of [21] to [23], wherein the hydrolysis product of a collagen further comprises Gly-X or X-Y that is the degradation product of a collagen tripeptide Gly-X-Y.

[25]
A collagen hydrolysis product for lowering blood cholesterol, containing at least one collagen tripeptide Gly-X-Y (where Gly-X-Y denotes an amino acid sequence in which X and Y denote amino acid residues other than Gly).

[26]
The collagen hydrolysis product of [25], wherein the hydrolysis product of a collagen comprises 25 to 100 mass % of the collagen tripeptide Gly-X-Y.

[27]
The collagen hydrolysis product of [25] or [26], wherein the collagen tripeptide Gly-X-Y is at least one peptide selected from the group consisting of Gly-Ala-Asp, Gly-Ala-Lys, Gly-Ala-Val, Gly-Pro-Gln, Gly-Pro-Met, Gly-Pro-Ile, Gly-Pro-Thr, Gly-Pro-Val, Gly-Ser-Hyp, Gly-Lys-Asp, Gly-Ala-Ala, Gly-Pro-Hyl, Gly-Leu-Hyp, Gly-Ala-Arg, Gly-Ala-Ser, Gly-Ala-Hyp, Gly-Gln-Glu, Gly-Glu-Gln, Gly-Pro-Ser, Gly-Pro-Lys, Gly-Pro-Ala, Gly-Pro-Pro, Gly-Pro-Arg and Gly-Pro-Hyp.

[28]
The collagen hydrolysis product of any one of [25] to [27], wherein the hydrolysis product of a collagen further comprises Gly-X or X-Y that is the degradation product of a collagen tripeptide Gly-X-Y.

Effects of the Invention

According to the present invention, provided are a new treatment (progression-inhibiting drug) and preventive drug for atherosclerosis, and a blood cholesterol-lowering drug that is effective to treatment, prevention and the like of atherosclerosis. The present invention further provides a functional food and a specific health food that are effective to inhibition and/or prevention vascular aging and inflammation. The collagen hydrolysis product containing a collagen tripeptide Gly-X-Y that is contained as an active ingredient in the progression-inhibiting drug, preventive drug, blood cholesterol-lowering drug, functional food, and specific health food of the present invention is a biologically derived, highly safe substance. It has the effect of inhibiting the migration and proliferation of smooth muscle cells and has the effects of inhibiting the initiation and progression of atherosclerosis itself. Thus, it is biologically safe and inhibits the development of atherosclerosis.

BRIEF DESCRIPTION OF THE DRAWINGS

FIG. 3A shows an SDS-PAGE electrophoretic image of PCNA expressed by AoSMCs 24 hours after exposure to CTP30.

FIG. 3B indicates the average±SD of the relative strength of the band (PCNA/tubulin).

FIG. 19-1 shows the total number of migrated cells during 24 hours of the administration of GELITA-SOL DA ("DA" hereinafter), with the number of migrated AoSMCs in the control group denoted as 100%. The values given are the relative averages±SD (percentage of control group) of four independent trials.

FIG. 19-2 shows the total number of migrated cells during 48 hours of the administration of DA, with the number of migrated AoSMCs in the control group denoted as 100%. The values given are the relative averages±SD (percentage of control group) of four independent trials.

FIG. 19-3 shows the total number of migrated cells during 24 hours of the administration of GELITA-SOL LDA Aggl. ("LDA" hereinafter), with the number of migrated AoSMCs in the control group denoted as 100%. The values given are the relative averages±SD (percentage of control group) of four independent trials.

FIG. 19-4 shows the total number of migrated cells after 48 hours of the administration of LDA, with the number of migrated AoSMCs in the control group denoted as 100%. The values given are the relative averages±SD (percentage of control group) of four independent trials.

FIG. 20-1 shows the effects of three concentrations (3, 30, 300 μg/mL) of DA on the proliferation of AoSMCs and the time-course change in the control group (0 μg/mL). The various concentrations of DA were administered to the AoSMCs for the periods indicated, after which the total number of cells in five high power fields (×200) was calculated. The values given are the averages±SD of three independent trials.

FIG. 20-2 shows the effects of three concentrations (3, 30, 300 μg/mL) of LDA on the proliferation of AoSMCs and the time-course change in the control group (0 μg/mL). The various concentrations of LDA were administered to the AoSMCs for the periods indicated, after which the total number of cells in five high power fields (×200) was calculated. The values given are the averages±SD of three independent trials.

FIG. 21-1 shows the effects of three concentrations (3, 30, 300 μg/mL) of DA on the ratio of PCNA-positive cells in AoSMCs and the effect on the control group (0 μg/mL). The values given are the averages±SD of three independent trials, and represent the ratio of PCNA-positive cells.

FIG. 21-2 shows the effects of three concentrations (3, 30, 300 μg/mL) of LDA on the ratio of PCNA-positive cells in AoSMCs and the effect on the control group (0 μg/mL). The values given are the averages±SD of three independent trials, and represent the ratio of PCNA-positive cells.

MODES OF CARRYING OUT THE INVENTION

Figure 1:
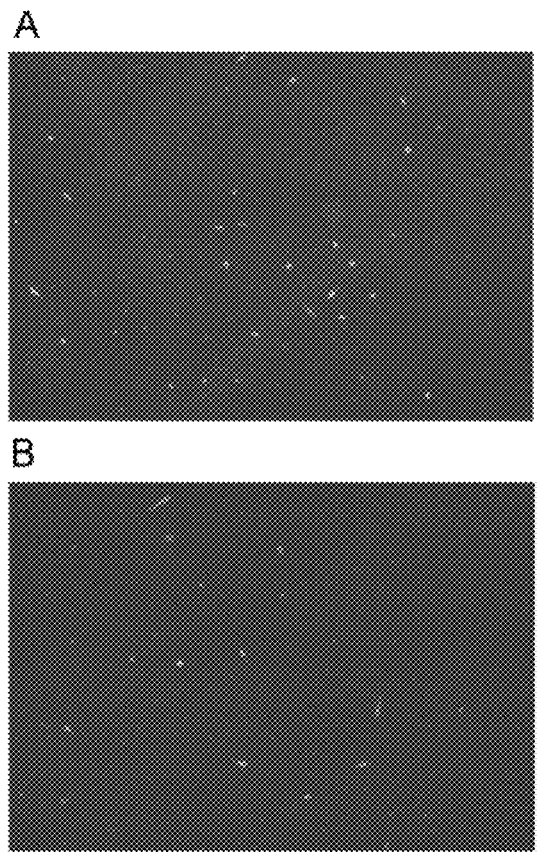
FIG. 1 shows the results of an experiment on the effect of CTP on the migration of human aortic smooth muscle cells (AoSMCs). It shows migrated AoSMCs in a lower power field in an inverted microscope. A is a control group and B is a group of CTP 3 μg/mL.

The Drug Inhibiting the Progression of Atherosclerosis

The first aspect of the present invention is a drug inhibiting the progression of atherosclerosis. Atherosclerosis occurs in relatively thick arteries such as the aorta, cerebral arteries, and coronary arteries. A viscous "gruel-like" substance comprised of lipids such as cholesterol and cholesterol esters accumulates on the intima of the artery, forming atheromatous plaque (gruel-like patches). These gradually thicken, causing the lumen of the artery to slowly narrow. The present invention inhibits the progression of atherosclerosis.

The drug inhibiting the progression of atherosclerosis of the present invention contains an active ingredient in the from of the hydrolysis product of a collagen containing at least one collagen tripeptide Gly-X-Y (where Gly-X-Y denotes an amino acid sequence in which X and Y denote amino acid residues other than Gly). The collagen hydrolysis product desirably comprises 25 to 100 mass % of the collagen tripeptide Gly-X-Y. When it is desirable to selectively achieve just the effect of a collagen tripeptide Gly-X-Y, the content of the collagen tripeptide Gly-X-Y is desirably higher. In such cases, it is desirably 30 to 100 mass %, preferably 50 to 100 mass %, and more preferably, falls within a range of 80 to 100 mass %. Because the drug that inhibits the progression of atherosclerosis of the present invention contains a collagen tripeptide Gly-X-Y, a high degree of purification is necessary to increase the purity of the collagen tripeptide Gly-X-Y to achieve the desired effect, tending to increase manufacturing costs. Accordingly, the content (purity) of the hydrolysis product of collagen containing a collagen tripeptide Gly-X-Y that is employed can be determined taking into account the desired effect and the cost (expense).

Further, the collagen tripeptide Gly-X-Y that is contained in the hydrolysis product of collagen can be at least one tripeptide selected from the group consisting of Gly-Ala-Asp, Gly-Ala-Lys, Gly-Ala-Val, Gly-Pro-Gln, Gly-Pro-Met, Gly-Pro-Ile, Gly-Pro-Thr, Gly-Pro-Val, Gly-Ser-Hyp, Gly-Lys-Asp, Gly-Ala-Ala, Gly-Pro-Hyl, Gly-Leu-Hyp, Gly-Ala-Arg, Gly-Ala-Ser, Gly-Ala-Hyp, Gly-Gln-Glu, Gly-Glu-Gln, Gly-Pro-Ser, Gly-Pro-Lys, Gly-Pro-Ala, Gly-Pro-Pro, Gly-Pro-Arg and Gly-Pro-Hyp. These tripeptides are almost all hydrophilic.

In addition to the above collagen tripeptide Gly-X-Y, the collagen hydrolysis product can contain other collagen hydrolysis products in the form of tetramer and higher hydrolysis products of amino acids of higher molecular weight than tripeptides, as well as degradation products of collagen tripeptides Gly-X-Y in the form of Gly-X and X-Y. Both Gly-X and X-Y are dipeptides, and X and Y denotes amino acid residues other than Gly. In the case of the CTP30 employed in the embodiments, the content of collagen tripeptides Gly-X-Y is 25 to 35 mass %, the content of Gly-X and X-Y is about 10 mass %, and the remainder is tetramer and higher hydrolysis products of amino acids of higher atomic weight than tripeptides. The maximum molecular weight of the tetramer and higher hydrolysis products of amino acids is about 6,000. That is clear from the HPLC chromatogram of CTP30 shown in FIG. 22. In the case of the CTP90 employed in the embodiments, the content of collagen tripeptides Gly-X-Y is 85 to 100 mass %. The remainder is comprised of Gly-X, X-Y, and tetramer and higher hydrolysis products of amino acids of greater molecular weight than tripeptides. That is clear from the HPLC chromatogram of CTP90 shown in FIG. 22.

The hydrolysis product of a collagen containing a collagen tripeptide Gly-X-Y is obtained by hydrolysis using bacterial collagenase (Patent References 8 and 9) that cuts the peptide bond of typed collagen at the amino terminus of glycine. The type of collagen tripeptide Gly-X-Y that is contained in the hydrolysis product of collagen differs with the hydrolysis conditions, the type of collagenase employed in hydrolysis, and the type of collagen employed as starting material in hydrolysis. The hydrolysis product can be purified by various methods to obtain a hydrolysis product containing nonantigenic and low-allergenic tripeptide fractions that have been highly purified and containing a collagen tripeptide (CTP) having a Gly-X-Y sequence.

In the drug inhibiting the progression of atherosclerosis of the present invention, the active ingredient in the form of a collagen hydrolysis product will vary based on the concentration of the collagen tripeptide Gly-X-Y contained in the collagen hydrolysis product. For example, a collagen hydrolysis product in which the concentration of collagen tripeptide Gly-X-Y is 30% can be administered orally all at once, or in two to three installments, each day in a dosage of 10 to 1,000 mg per kg of body weight. The collagen hydrolysis product that is the active ingredient can be in the form of a powder, tablet, or aqueous solution. There is no limitation to oral administration; injections and the like can also be employed.

The Preventive Drug for Atherosclerosis

The second aspect of the present invention is a preventive drug for atherosclerosis. Atherosclerosis occurs in relatively thick arteries such as the aorta, cerebral arteries, and coronary arteries. A viscous "gruel-like" substance comprised of lipids such as cholesterol and cholesterol esters accumulates on the intima of the artery, forming atheromatous plaque (gruel-like patches). These gradually thicken, causing the lumen of the artery to slowly narrow and clinical symptoms to appear. The present invention prevents the onset of atherosclerosis.

The hydrolysis product of a collagen contained as an active ingredient in the preventive drug for atherosclerosis of the present invention is identical to that described for the progression-inhibiting drug above.

Although varying with the concentration of the active ingredient in the form of the collagen tripeptide Gly-X-Y that is contained in the collagen hydrolysis product, the preventive drug for atherosclerosis of the present invention can be administered orally all at once, or in two to three installments, each day in a dosage of 10 to 1,000 mg per kg of body weight in the case of a collagen hydrolysis product with a collagen tripeptide Gly-X-Y concentration of 30%, for example. The collagen hydrolysis product that is the active ingredient can be in the form of a powder, tablet, or aqueous solution. There is no limitation to oral administration; injections and the like can also be employed.

The method of inhibiting the progression of, or preventing, atherosclerosis that comprises administering to a patient an effective quantity of the decomposition product of a collagen containing at least one collagen tripeptide Gly-X-Y (where Gly-X-Y denotes an amino acid sequence in which X and Y denote amino acid residues other than Gly) of the present invention can also be implemented based on the description set forth above. The hydrolysis product of a collagen containing at least one collagen tripeptide Gly-X-Y (where Gly-X-Y denotes an amino acid sequence in which X and Y denote amino acid residues other than Gly) for use in inhibiting the progression of, or preventing, atherosclerosis of the present invention can also be implemented based on the description set forth above.

The Blood Cholesterol-Lowering Drug

The third aspect of the present invention is a blood cholesterol-lowering drug. Atherosclerosis occurs in relatively thick arteries such as the aorta, cerebral arteries, and coronary arteries. A viscous "gruel-like" substance comprised of lipids such as cholesterol and cholesterol esters accumulates in the intima of the artery, forming atheromatous plaque (gruel-like patches). These gradually thicken, causing the lumen of the artery to slowly narrow and clinical symptoms to appear. The present invention lowers blood cholesterol. As a result, it prevents or inhibits the onset of various disorders caused by blood cholesterol, such as atherosclerosis.

The hydrolysis product of a collagen contained as an active ingredient in the blood cholesterol-lowering drug of the present invention is identical to that described for the progression-inhibiting drug above.

Although varying with the concentration of the active ingredient in the form of the collagen tripeptide Gly-X-Y that is contained in the collagen hydrolysis product, the preventive drug of the blood cholesterol-lowering drug of the present invention can be administered orally all at once, or in two to three installments, each day in a dosage of 10 to 1,000 mg per kg of body weight in the case of a collagen hydrolysis product with a collagen tripeptide Gly-X-Y concentration of 30%, for example. The collagen hydrolysis product that is the active ingredient can be in the form of a powder, tablet, or aqueous solution. There is no limitation to oral administration; injections and the like can also be employed.

The method of lowering the blood cholesterol that comprises administering to a patient an effective quantity of the decomposition product of a collagen containing at least one collagen tripeptide Gly-X-Y (where Gly-X-Y denotes an amino acid sequence in which X and Y denote amino acid residues other than Gly) of the present invention can also be implemented based on the description set forth above. The hydrolysis product of a collagen containing at least one collagen tripeptide Gly-X-Y (where Gly-X-Y denotes an amino acid sequence in which X and Y denote amino acid residues other than Gly) for lowering brood cholesterol of the present invention can also be implemented based on the description set forth above.

The Functional Food and Specific Health Food

The present invention includes a functional food and a specific health food that is effective to inhibition and/or prevention of vascular aging and inflammation, and that contain an active ingredient in the form of the hydrolysis product of a collagen containing at least one collagen tripeptide Gly-X-Y (where Gly-X-Y denotes an amino acid sequence in which X and Y denote amino acid residues other than Gly).

As stated above, the initial pathological change associated with atherosclerosis is observed in most children when they reach an age somewhere between 2 and 15. The increase in pathological change becomes marked with the attainment of adolescence. About 30% of the arterial surfaces undergo pathological change by the age of 20 to 30 (Nonpatent Reference 6). The functional food and specific health food of the present invention is effective to inhibition and/or prevention vascular aging and inflammation, and can thus be employed by the large number of people who need to inhibit the progression of, or prevent, atherosclerosis. The type of collagen tripeptide Gly-X-Y that is contained in the functional food and specific health food of the present invention is identical to that employed in the progression-inhibiting drug and preventive drug for atherosclerosis. Examples of functional foods and specific health foods are supplements such as tablets, capsules, and drinks comprising an active ingredient in the form of the hydrolysis product of a collagen containing at least one collagen tripeptide Gly-X-Y. Further examples are foods and drinks into which have been blended the same collagen hydrolysis product. The functional food and specific health food of the present invention are effective to inhibition of the progression of, and prevent, atherosclerosis, and can thus be employed by the large number of people who need to inhibit the progression of, or prevent, atherosclerosis.

The concentration of the collagen hydrolysis product in the functional food and specific health food is desirably 15 mass % or greater based on the collagen tripeptide Gly-X-Y. As stated above, the progression-inhibiting and preventive effects on atherosclerosis of the present invention are achieved using the hydrolysis product of a collagen containing a collagen tripeptide Gly-X-Y. They require purifying the collagen tripeptide Gly-X-Y to a high degree, which tends to increase the cost. However, in hydrolysis products of collagen with a low concentration of the collagen tripeptide Gly-X-Y, components other than the collagen tripeptide Gly-X-Y, particularly high-molecular-weight components with low degrees of hydrolysis, sometimes increase, compromising their addition to foods. Accordingly, the purity of the hydrolysis product of a collagen containing the collagen tripeptide Gly-X-Y that is employed can be suitably determined by taking into account the desired cost (expense) and effect, and the ease of addition to foods. In functional foods, it is sometimes desirable to keep the price down. In such cases, the content of the collagen tripeptide Gly-X-Y is desirably 15 to 25 mass %. In specific health foods, as well, the content of collagen tripeptide Gly-X-Y can be 15 to 25 mass % in the same manner as for functional foods. However, there are cases where it is desirable to achieve a more pronounced effect than in functional foods. In such cases, the content of the collagen tripeptide Gly-X-Y is desirably 25 to 35 mass %.

Although varying with the concentration of the active ingredient in the form of the collagen tripeptide Gly-X-Y that is contained in the collagen hydrolysis product, the functional food of the present invention can be administered orally all at once, or in two to three installments, each day in a dosage of 10 to 1,000 mg per kg of body weight in the case of a collagen hydrolysis product with a collagen tripeptide Gly-X-Y concentration of 20%, for example. The form of the functional food of the present invention is not specifically limited. It can be a solid, liquid, fluid (such as a gel or paste), or the like. Nor is there a limitation with regard to the type of food. Since the collagen hydrolysis product that is the active ingredient can be readily applied as a solid, liquid, or fluid, for example, it can be a powder or liquid (such as an aqueous solution or aqueous dispersion). The functional food of the present invention inhibits the vascular changes that accompany age, and in particular, inhibits atherosclerosis and vascular inflammation, functioning to maintain blood vessels in good condition.

Although varying with the concentration of the active ingredient in the form of the collagen tripeptide Gly-X-Y that is contained in the collagen hydrolysis product, the specific health food of the present invention can be administered orally all at once, or in two to three installments, each day in a dosage of 10 to 500 mg per kg of body weight in the case of a collagen hydrolysis product with a collagen tripeptide Gly-X-Y concentration of 20%, for example. The form of the specific health food of the present invention is not specifically limited. It can be a solid, liquid, fluid (such as a gel or paste), or the like. Nor is there a limitation with regard to the type of food. In the same manner as for the above medicinal drugs, it can be formulated as a tablet, capsule, or drink. Depending on the form of the food, the collagen hydrolysis product that is the active ingredient can be a powder or liquid (such as an aqueous solution or aqueous dispersion). The specific health food of the present invention is effective to inhibition, and/or prevention, of vascular aging and inflammation, and is thus useful to people who are concerned about atherosclerosis or vascular aging, and to people who would like to prevent or reduce atherosclerosis or vascular aging. A specific health food is generally a food that is sold with an indication of a specific health application of the food. The specific health food of the present invention is a food that is expected to be sold with the indication that it prevents or reduces atherosclerosis or vascular aging.

EMBODIMENTS

The present invention will be described in greater detail below based on embodiments.

Embodiment 1

The Experimental Method of Cultivation of Smooth Muscle Cells

Human aortic smooth muscle cells (AoSMCs) were maintained in a 5% $CO_2$ environment at 37° C. in a SmGM-2 Bullet Kit (Cambrex, CC-3182) containing basic medium (SmBM, CC-3181) and SingleQuots (CC-4149) procured from Lonza Walkerville (US, product code CC-2571). The cells were grown in collagen-coated culture dishes 10 cm in diameter in a 5% $CO_2$ incubator at 37° C. When the cells reached a density of 70 to 80% and numerous mitotic figures appeared throughout the dish, cells were subcultured using Hank's balanced salt solution (HBSS) containing 0.025% trypsin and 0.01% EDTA. Following treatment with trypsin, the cells were suspended in media that contained 5% fetal bovine serum (FBS) and media that did not for use in subsequent experiments.

Testing for AoSMC Migration

AoSMC migration was tested with Transwell Permeable Supports (Corning Incorporated Life Sciences, U.S. Pat. No. 3,422) having a membrane filter (6.5 mm in diameter) with a pore diameter of 8.0 μm. AoSMCs that had been cultured for 24 hours in SmBM medium were treated with trypsin and suspended in SmBM to a concentration of $1 \times 10^6$ cells/mL. A 100 μL quantity of the cell suspension was placed in the upper compartment, and SmGM 650 μL containing CTP30 (collagen tripeptide content 30%) in various concentrations (0, 3, 30, 300 μg/mL) was placed in the lower compartment. The transwells were incubated in a 5% $CO_2$ incubator at 37° C. Following incubation for 12 hours, 24 hours, and 48 hours, the upper compartment was removed. The AoSMCs that had migrated through the holes of the membrane filter into the lower compartment and attached to the bottom of the lower compartment were immobilized with 4% paraformaldehyde and then calculated with an inverted microscope (400× magnifications) to quantify the AoSMC migration.

Western Blot Assay for PCNA in AoSMCs

AoSMCs that had been suspended to a concentration of $1 \times 10^5$ cells/mL were distributed to a six well microplate (5 mL/well). Following adhesion, the medium was replaced with SmGM containing various concentrations (0, 3, 30, 300 μg/mL) of CTP30. After incubation for 24 hours, the cells were collected for a Western blot assay as set forth below. The cell medium was washed twice with phosphate buffer physiological saline, and then lysed on ice in a lysis buffer solution (50 mM Tris-HCl, 150 mM NaCl, 1.0% Nonidet P40) to which a protease inhibitor cocktail (Completemini, EDTA free, Roche) had been added, and centrifugally separated at 12,000 g for 20 minutes at 4° C. The supernatant was added to a sample buffer solution and immediately mixed. The protein concentration was measured with a bicinchoninic acid protein assay reagent. An equal quantity of protein (30 μg) was isolated by 10% SDS-PAGE and blotted with Immobilon transfer membrane (Millipore, US). The transfer membrane was blocked at 25° C. for one hour with Tris buffer physiological saline containing 3% bovine serum albumin. A primary antibody (anti-human PCNA antibody, 1:500) was then used to conduct a reaction. HRP-conjugated goat anti-mouse IgG (Pierce, US) and SuperSignal West Femto maximum sensitivity substrate (Pierce, US) was used to detect the primary antibody. The resulting chemiluminescence was captured with a cooled CCD camera system (ATTO) and quantified by densitometry analysis ImageJ software (NIH Image).

Testing of PCNA-Positive Ratio in AoSMCs

AoSMCs were treated with trypsin and suspended in SmGM medium to a concentration of $1 \times 10^5$ cells/mL. Sterile cover slices were put into a six-well microplate, after which the cell suspension was distributed in the wells (5 mL cells/well). Following adhesion (about six hours after distribution), the medium was replaced with SmGM containing various concentrations (0, 3, 30, 300 μg/mL) of CTP30. Following incubation for 24 hours, the slices were removed and PCNA immunocytochemistry was conducted with monoclonal mouse anti-human PCNA antibody (Dako Japan, Japan, M0879) and SAB-PO kit (Histofine, Japan, code 424022). And then, the slices were double stained with hematoxylin, dehydrated, and tightly sealed. The cells were then calculated under a microscope. Ten high power fields (200× magnification) were selected for each slice and the total number of cells and the number of PCNA-positive cells were calculated (PCNA-positive ratio=number of positive cells/total number of cells).

AoSMC Proliferation Testing

AoSMCs suspended in SmGM medium to a concentration of 1×10$^5$ cells/mL was distributed to a six-well microplate in which a sterile cover slice had been placed in each well. Following adhesion, the medium was replaced with SmGM containing various concentrations (0, 3, 30, 300 μg/mL) of CTP30. The cells were cultured for 0 hour, 24 hours, 48 hours, and 72 hours. Then the slices were removed, and fixed with 4% paraformaldehyde, and stained with hematoxylin, and subsequently dehydrated and sealed. The cells were then counted under a microscope. Five high power fields (200× magnification) were selected for each slice and the total number of cells was calculated.

Data Analysis and Statistical Evaluation

The data were analyzed with the statistical package of Social Sciences 10.0 statistical software. The statistical significance between groups was determined by a least significant difference post hoc test following a one-way ANOVA.

Results

The Effect of CTP on Migration of AoSMCs

Figure 2:
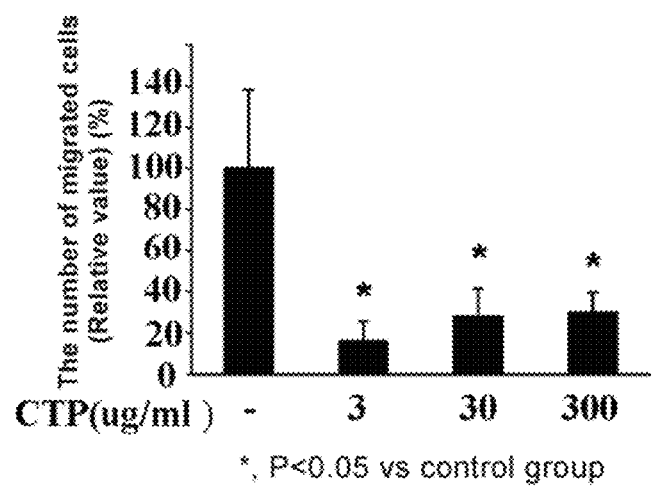
FIG. 2 shows the results of the effect of CTP30 at various concentrations on the migration of human aortic smooth muscle cells (AoSMCs). The results are given as percentages relative to the number of migrated cells in a control group (CTP30: 0 μg/mL).

Following the administration of various concentrations of CTP30, no obvious migration of AoSMCs was observed at 12 hours, and only extremely slight migration was found at 24 hours (the results were not shown). FIG. 1 shows the picture of the migrated cells at 48 hours. Many migrated cells that appeared in the typical spindle-shape adhered to the bottom surface of the wells of the lower compartment were detected by inverted microscopy. FIG. 2 shows the effect of CTP30 on AoSMC migration. At 48 hours, CTP30 administered at the three concentrations of (3, 30, 300 μg/mL) strongly inhibited AoSMC migration. However, no significant difference was found between the different concentrations of CTP30.

FIGS. 1 and 2 show the effects of various concentrations of CTP30 on the migration of human aortic smooth muscle cells (AoSMCs). The various concentrations of CTP30 were administered to AoSMCs for 48 hours, after which the number of migrated cells was calculated. (FIG. 1): Migrated AoSMCs in a low power field under an inverted microscope. A and B denote the control group and CTP30 3 μg/mL group, respectively. (FIG. 2): Each value indicates the relative average±SD (percentage of the control group) counted in four independent trials, with the number of smooth muscle cells that migrated in the control group (CTP 0 μg/mL) being denoted as 100%.

The Effect of CTP on PCNA Protein Expression in AoSMCs

Figure 3:
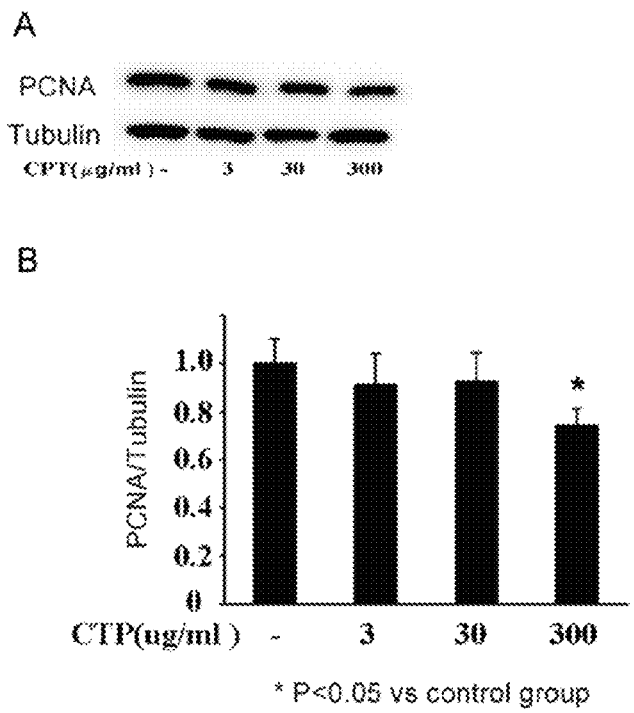
FIG. 3 shows the results of an experiment on the effect of CTP30 on the expression of the PCNA protein of AoSMCs.

FIG. 3A shows an electrophoretic image by SDS-PAGE of the PCNA expressed by AoSMCs following 24 hours of exposure to CTP30. In the course of conducting quantitative analysis by densitometry, it was discovered that 300 μg/mL of CTP30 clearly inhibited the expression of PCNA in AoSMCs compared to the control group. However, this effect was not detected in the 3 μg/mL CTP group or the 30 μg/mL group (as shown in FIG. 3). These results indicated that suppression of the expression of PCNA in AoSMCs occurred strongly 24 hours after the administration of a high concentration of CTP30.

FIG. 3 shows the effect of various concentrations of CTP30 on the expression of PCNA in human aortic smooth muscle cells (AoSMCs). Various concentrations of CTP30 were administered for 24 hours to AoSMCs. Subsequently, Western blotting was conducted in the manner described in the above test method. (FIG. 3A) An SDS-polyacrylamide gel (10%) electrophoretic image of PCNA in AoSMCs. FIG. 3B): Each value is the average of three independent trials and indicates the average±SD of the relative strength of the band (PCNA/tubulin).

The Effect of CTP on the PCNA-Positive Cell Ratio in AoSMCs

Figure 4:
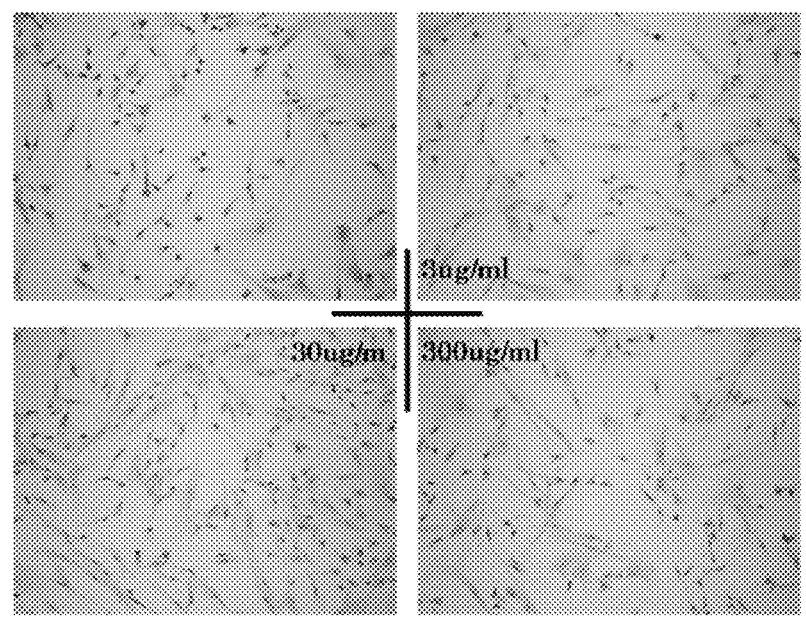
FIG. 4 shows the results of an experiment on the effects of CTP30 on the PCNA-positive ratio in human aortic smooth muscle cells (AoSMCs). The PCNA-positive AoSMCs exhibited brown-color nuclei and the PCNA-negative AoSMCs exhibited blue nuclei in the immunocytochemistry.

To determine whether the change of PCNA expression found by Western blotting was a result of down-regulation in the whole cells level or resulted from a reduction in the PCNA-positive cell ratio, the PCNA immunocytochemistry was employed and the positive ratio was calculated. FIG. 4 shows the respective immunocytochemistry results for various CTP30 concentrations. In the figure, the brown-color nuclei and fine spindle shape of PCNA-positive cells can be seen. At the same time, PCNA-negative cells exhibit blue-color nuclei and an irregular form with broad cytoplasm. The quantitative analysis shown in FIG. 5 clearly indicates that the PCNA-positive ratio decreased markedly after 24 hours of administration of CTP30. At the same time, there was no significant difference between the three groups of various concentrations, indicating that the effect at 24 hours was not clearly dependent on dosage.

Figure 5:
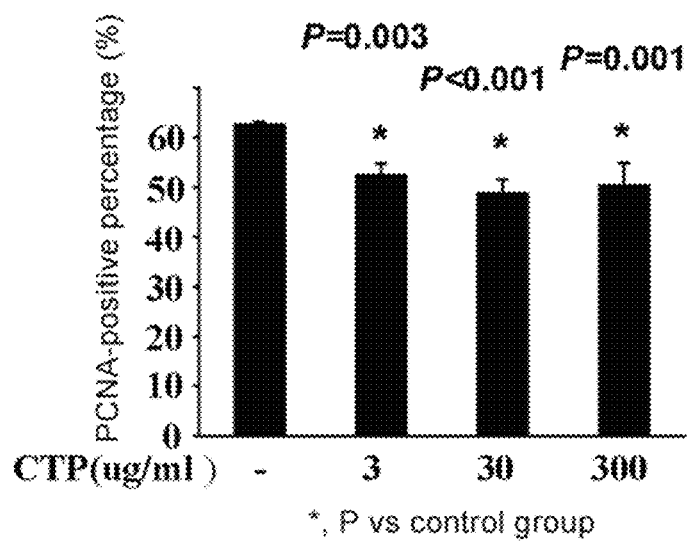
FIG. 5 shows the results of an experiment on the effects of CTP30 on the PCNA-positive ratio in human aortic smooth muscle cells (AoSMCs). The ratio of PCNA-positive cells is given (average±SD).

FIGS. 4 and 5 show the effects of various concentrations of CTP30 on the PCNA-positive ratio in human aortic smooth muscle cells (AoSMCs). Various concentrations of CTP30 were administered to AoSMCs for 24 hours. Subsequently, as described for the above test method, the PCNA immunocytochemistry was employed and the positive ratio was calculated in 10 high power fields (200×). (FIG. 4) PCNA-positive AoSMCs (brown-color nuclei) and PCNA-negative AoSMCs (blue-color nuclei) by the immunocytochemistry. (FIG. 5): Each value is the average±SD of three independent trials and denotes the ratio of PCNA-positive cells.

The Time-Course Effect of CTP on AoSMC Proliferation

Figure 6:
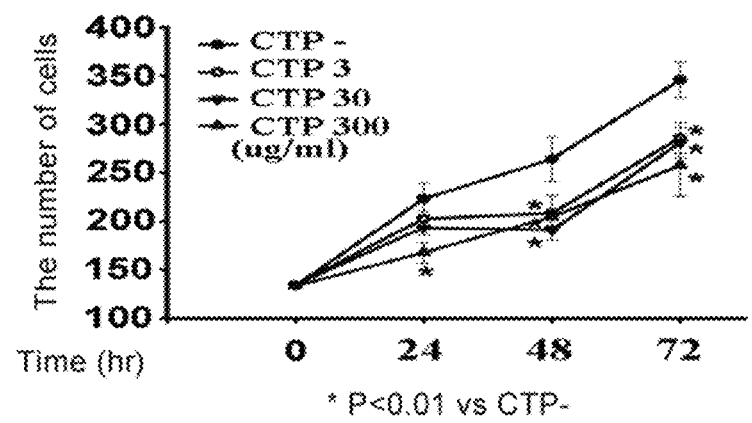
FIG. 6 shows the time-course change in the effect of CTP30 at various concentrations on the proliferation of human aortic smooth muscle cells (AoSMCs). Various concentrations of CTP30 were administered to AoSMCs for the periods indicated, and the total number of cells in five high power fields (200×) was calculated. Each value is the average±SD of three independent trials.

Based on the graph shown in FIG. 6, the CTP30 300 μg/mL group exhibited a clear inhibitory effect on the proliferation of AoSMCs relative to the control group 24 hours after the administration of CTP30. However, no clear inhibitory effect was exhibited in the CTP30 3 μg/mL group or in the CTP30 30 μg/mL group. However, 48 hours and 72 hours after the administration of CTP30, the difference between the CTP30 high concentration group (300 μg/mL) and low concentration groups (3 μg/mL and 30 μg/mL) decreased, and all of the CTP groups exhibited clear inhibitory effects relative to the control group. Further, the various groups of cells exhibited a tendency toward continuous proliferation relative to the number of cells at the beginning, so the possibility of CTP30 having a toxic effect on AoSMCs could be ruled out.

FIG. 6 shows the time-course change of the effect of the various concentrations of CTP30 on the proliferation of human aortic smooth muscle cells (AoSMCs). Various concentrations of CTP30 were administered over the times indicated to AoSMCs. Subsequently, as described for the above test method, the total number of cells in five high power fields (200×) was calculated. Each value is the average±SD of three independent trials.

Discussion

It is well known that the migration of arterial medial smooth muscle cells into the intima and proliferation is one of the principal processes that cause atherosclerosis, along with the emigration and proliferation of macrophages and T lymphocytes. Following the injury of arterial endothelial cells, smooth muscle cells (SMCs) migrate from the media to the intima and proliferate in the intima. In the intima, the smooth muscle cells synthesize collagen fiber and elastic fiber. Further, some of the cells take up lipids and transform into foam cells. Accordingly, the smooth muscle cells, collagen fiber synthesized by smooth muscle cells, and other extracellular matrix components become the main components of atheromatous plaque. Many basic and clinical studies indicate that the proliferation and migration of SMCs greatly impact treatment effects, and directly impact long-term effects. The migration to and proliferation in the intima by smooth muscle cells, such as takes place with percutaneous transluminal coronary angioplasty (PTCA), a common method of treating atherosclerotic stenosis of the coronary arteries, is the principal cause of postangioplasty restenosis. Thus, how this process is regulated and how to inhibit the migration and proliferation of SMCs have assumed greater importance not only in basic medicine, but also in the clinical therapeutic field.

The above experimental results show for the first time the effect of CTP30 on the proliferation and migration of aortic media-derived smooth muscle cells (AoSMCs). Based on these results, it will be understood that CTP30 also has a marked inhibitory effect on not just the proliferation of human AoSMCs in vitro, but also on their migration. Three different concentrations of CTP30 and CTP90, which have different contents of CTP, all exhibited the same effects and a tendency to inhibit. Twenty-four hours after the administration of CTP, the CTP30 300 µg/mL group significantly lowered the total PCNA expression level and inhibited cell proliferation. In CTP30, with its low CTP content, the 3 µg/mL group and 30 µg/mL group did not exhibit a significant inhibiting effect at that time (24 hours), but did exhibit significant proliferation-inhibiting effects at culture times of 48 hours and 72 hours. This suggests that the inhibiting effect appears more rapidly at high concentration than at low concentration, and this dosage dependence only exists during the initial period (24 hours) of culturing. The fact that CTP90, with its high CTP content, significantly inhibited cell proliferation just 24 hours after administration even at low concentrations (3 µg/mL, 30 µg/mL) supports the above.

Proliferating cell nuclear antigen (PCNA) was first identified as an antigen that was detected in the nuclei of cells during the DNA synthesis phase (S phase) of the cell cycle and reacted to antibody in the serum of patients with autoimmune disease (SLE). It was used as an index of cell proliferation. Humbert et al. indicated the PCNA intensity at different times in the S phase on a three-dimensional display, showed that the PCNA expression level varied greatly at different times, and demonstrated that it was high during the middle period of the S phase and low during the initial and late periods (Reference Document 1-1). The above experimental results indicate that 24 hours of administering CTP30 induced a reduction in the PCNA-positive ratio in the low-concentration groups (3 µg/mL and 30 µg/mL). However, neither the PCNA expression level nor the number of cells exhibited a reduction in either group. The present inventors believe that there was a time lag in the PCNA protein expression level and actual cell mitosis and proliferation based on the identification of PCNA-positive cells by immunocytochemistry and Western blotting analysis.

The proliferation and migration of SMCs is a complex process involving the expression of various genes and related proteins, such as transcription factors, cyclins, cyclin-dependent kinases (Cdks), and adhesion molecules. Thus far, relations have been reported between fibrillar collagen or degraded collagen fragments and the growth and migration of smooth muscle cells. The fact that fibrous collagen can inhibit the proliferation of arterial smooth muscle cells through regulation of Cdk2 inhibiting factor (Reference Document 1-2) and the fact that fibrous collagen specifically regulates human arterial smooth muscle cell genes involved in cellular response and the pericellular matrix environment (Reference Document 1-3) have been reported. However, the underlying mechanism whereby CTP inhibits proliferation and migration of smooth muscle cells is unknown currently.

The present experimental results indicate that CTP significantly inhibits human AoSMC proliferation and migration in vitro, and can lower the PCNA expression level and PCNA positive-cell ratio. At the same time, such inhibiting effects do not present clear dosage dependence or cell toxicity. The present results strongly suggest that CTP is an effective regulatory factor for the migration and proliferation of human arterial smooth muscle cells, and suggest that CTP can be employed as a therapeutic drug for cardiovascular diseases.

REFERENCE DOCUMENTS CITED IN EMBODIMENT 1

(1-1) HUMBERT C, SANTISTEBAN M S, USSON Y, ROBERT-NICOUD M: *Intranuclear co-location of newly replicated DNA and PCNA by simultaneous immunofluorescent labelling and confocal microscopy in MCF-7 cells*. J Cell Sci. 1992 103: 97-103

(1-2) Koyama H, Raines E W, Bornfeldt K E, Roberts J M, Ross R. *Fibrillar collagen inhibits arterial smooth muscle cell proliferation through regulation of Cdk2 inhibitors*. Cell 1996; 87: 1069-1078

(1-3) Ichii T, Koyama H, Tanaka S, Kim S, Shioi A, Okuno Y, Raines E W, Iwao H, Otani S, Nishizawa Y. *Fibrillar collagen specifically regulates human vascular smooth muscle cell genes involved in cellular responses and the pericellular matrix environment*. Circ Res. 2001; 88: 460-467

The disclosures of the above cited Reference documents 1-1 to 1-3 are expressly incorporated herein by reference in their entirety.

Embodiment 2

Figure 7:
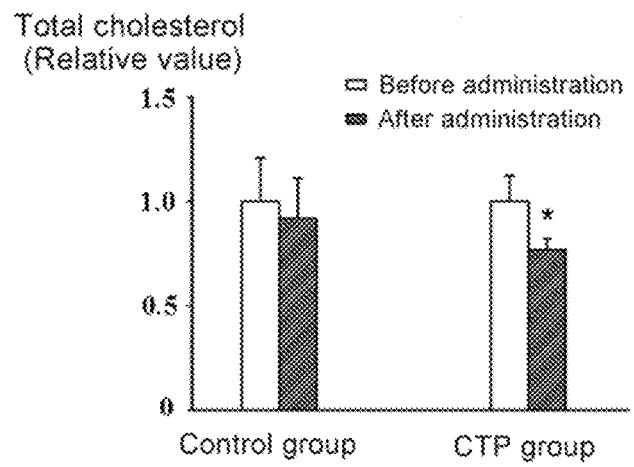
FIG. 7 shows the results of a comparison of the serum total cholesterol level of the control group and the group administered CTP30 in Embodiment 2.

Five familial hypercholesterolemic model rabbits (KHC rabbits, body weight about 2 kg, three months old, birth location: Japan Laboratory Animals, Inc., Tokyo, purchased from Sankyo Labo Service Corporation, Inc., Toyama) were orally administered 200 mg/kg of CTP30 (obtained by dissolving 400 mg of CTP30 in 5 mL of distilled water (Milli-Q)) for three months. Their total blood cholesterol levels were compared with those of five rabbits in a control group administered distilled water to which no CTP was added. The results are given in FIG. 7. Compared to three months earlier, the control group exhibited an 8% decrease in total blood cholesterol. By contrast, the CTP30-administered group exhibited a decrease of 23.2%, indicating that CTP had a clear total blood cholesterol-lowering effect.

Figure 8:
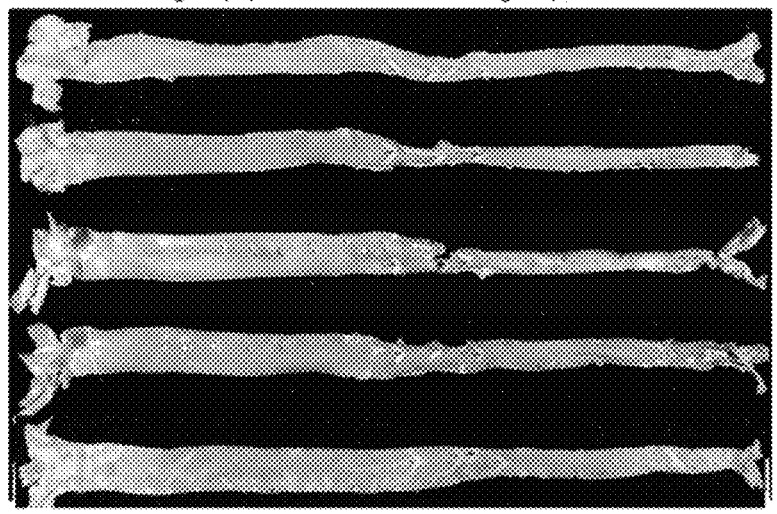
FIG. 8 shows a macroscopic photograph of inner surface of the aortas of the CTP30-administered group.
Figure 9:
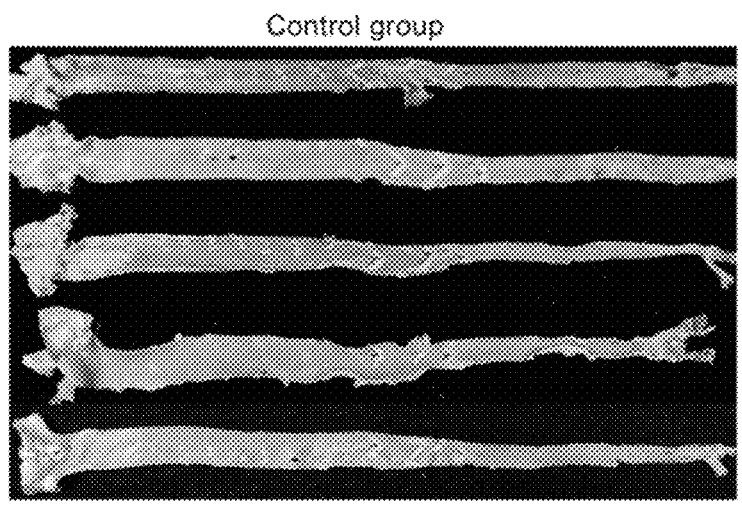
FIG. 9 shows a macroscopic photograph of inner surface of the aortas of the control group.
Figure 10:
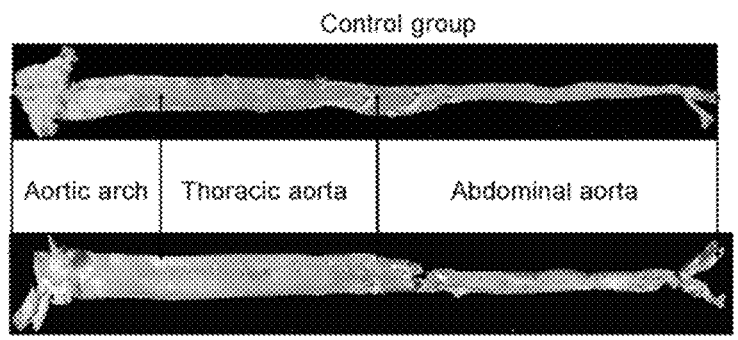
FIG. 10 shows three regions (from the left, the aortic arch, the thoracic aorta, and the abdominal aorta) of the aorta based on the area of pathological change (plaque) due to atherosclerosis.

The rabbits were then sacrificed and their aortas were observed. FIG. 8 shows a macroscopic photograph of the aortas of the CTP-administered group. FIG. 9 shows a macroscopic photograph of the aortas of the control group. FIG. 10 shows the area of pathological change (plaque) caused by atherosclerosis. Data obtained for each of three regions are given in Table 1 below. Specifically, the areas (i.e. based on digital camera images, the areas of the images of the diseased loci were converted to numbers based on the number of pixels, and the ratio to the area of the surface of the aorta was denoted as a percentage) of atherosclerotic loci (plaque) in three regions were compared. As a result, the control group had produced plaque over 16.4% of the total aortic area, but the extent of plaque was only 4.5% in the CTP-administered group. This amounted to only 27.4% of the plaque area produced in the control group, indicating that plaque development had been strongly inhibited.

TABLE 1

Percentage of Plaque (plaque area, %)

|  |  | Aortic arch, % | Thoracic aorta, % | Abdominal aorta, % | Total aorta, % |
| --- | --- | --- | --- | --- | --- |
| Control group n = 5 | Rabbit 1 | 49.6 | 6.3 | 3.5 | 15.6 |
|  | Rabbit 2 | 25.4 | 4.6 | 3.3 | 10.2 |
|  | Rabbit 3 | 65.9 | 8.4 | 2.5 | 27.1 |
|  | Rabbit 4 | 41.7 | 8.1 | 1.8 | 17.3 |
|  | Rabbit 5 | 32.3 | 4.7 | 3.4 | 11.9 |
|  | Mean ± SD | 43.0 ± 14.1 | 6.4 ± 1.6 | 2.9 ± 0.7 | 16.4 ± 5.9 |
| CTP group n = 5 | Rabbit 6 | 13.6 | 1.5 | 0.7 | 5.2 |
|  | Rabbit 7 | 12.2 | 2.0 | 1.2 | 5.0 |
|  | Rabbit 8 | 7.2 | 1.3 | 3.0 | 3.7 |
|  | Rabbit 9 | 21.1 | 2.3 | 1.3 | 6.8 |
|  | Rabbit 10 | 3.7 | 1.6 | 1.1 | 1.9 |
|  | Mean ± SD | 11.6 ± 5.9 | 1.7 ± 0.4 | 1.5 ± 0.8 | 4.5 ± 1.6 |
| P value vs control |  | 0.00340** | 0.00048** | 0.02341** | 0.00467** |

Embodiment 3

The Effect of CTP90 (Collagen Tripeptide Content 90%) on the Migration and Proliferation of Cultured Smooth Muscle Cells Experimental Method Smooth muscle cell migration and proliferation testing was conducted by the same method as for CTP30 set forth above.

Results

The Effect of CTP90 on AoSMC Migration

Figure 11:
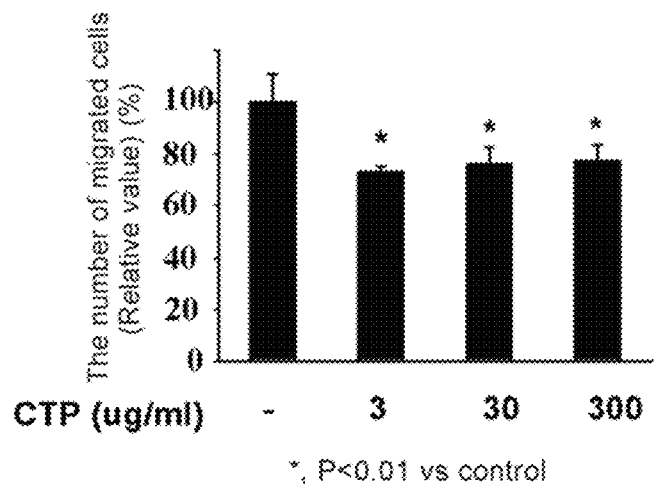
FIG. 11 shows the results of the effect of CTP90 at various concentrations on the migration of human aortic smooth muscle cells (AoSMCs). Percentages relative to the number of migratory cells in the control group (CTP90: 0 μg/mL) are given.

Following the administration of various concentrations of CTP90, no obvious migration of AoSMCs was observed at 12 hours, and only extremely slight migration was found at 24 hours (the results were not shown). FIG. 11 shows the effect of CTP90 on AoSMC migration. After 48 hours of administration, CTP90 administered at the three concentrations of (3, 30, 300 µg/mL) inhibited AoSMC migration. However, no significant difference was found between the different concentrations of CTP90.

FIG. 11 shows the effects of various concentrations of CTP90 on the migration of human aortic smooth muscle cells (AoSMCs). The various concentrations of CTP90 were administered to AoSMCs for 48 hours, after which the number of migrated cells was calculated. (FIG. 11) Each value indicates the relative average±SD (percentage of the control group) in four independent trials, with the number of smooth muscle cells that migrated in the control group being denoted as 100%.

The Effect of CTP90 on the PCNA-Positive Cell Ratio in AoSMCs

Figure 12:
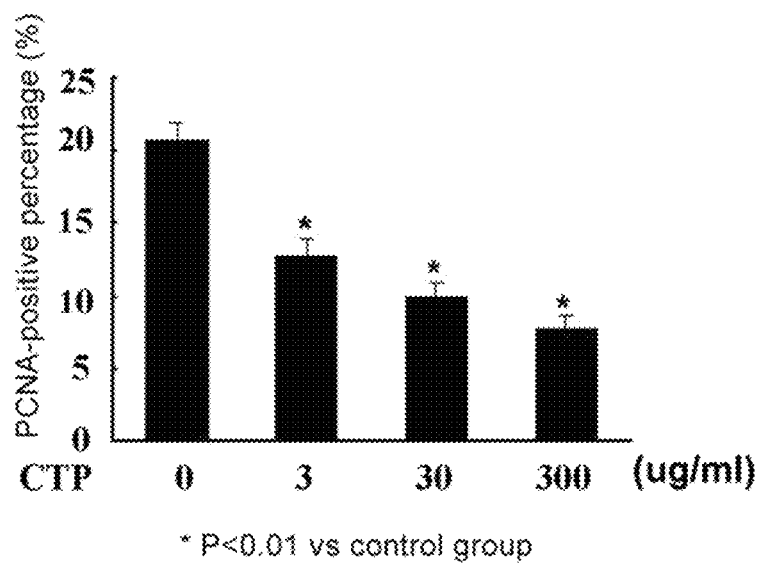
FIG. 12 shows the results of an experiment on the effect of CTP90 on the PCNA-positive ratio of human aortic smooth muscle cells (AoSMCs). The ratio of PCNA-positive cells (average±SD) is given.

FIG. 12 shows the effect of various concentrations of CTP90 on the PCNA-positive ratio in human aortic smooth muscle cells (AoSMC). Various concentrations of CTP90 were administered for 24 hours to AoSMCs. Subsequently, as described in the above experimental method, the PCNA immunocytochemical method was implemented and the positive ratio in 10 high power fields (200×) was calculated. Each value in FIG. 12 denotes the average±SD of the ratio of PCNA-positive cells in three independent trials.

The Time-Course Effect of CTP on AoSMC Migration

Figure 13:
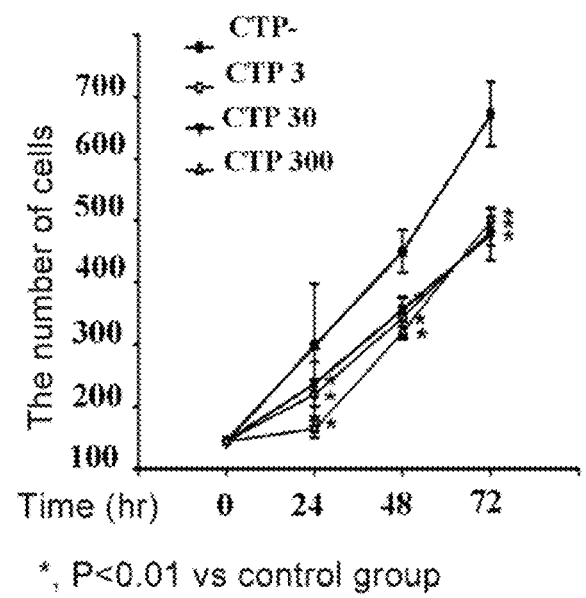
FIG. 13 shows the time-course change in the effect of CTP90 at various concentrations on the proliferation of human aortic smooth muscle cells (AoSMCs). Various concentrations of CTP90 were administered to AoSMCs for the periods indicated, and the total number of cells in five high power fields (200×) was calculated. Each value is the average±SD of three independent trials.

Based on the graph shown in FIG. 13, all of the CTP groups (3, 30, 300 µg/mL) exhibited clear inhibitory effects on the proliferation rate relative to the control group at 24 hours, 48 hours, and 72 hours following the administration of CTP90. Further, each group of cells tended to exhibit continuous proliferation relative to the number of cells at the onset, making it possible to rule out a toxic effect by CTP90 on AoSMCs.

FIG. 13 shows the time-course change in the effect of the various concentrations of CTP90 on the proliferation of human aortic smooth muscle cells (AoSMCs). Various concentrations of CTP90 were administered for the indicated periods to AoSMCs. Subsequently, as described for the experimental method above, the total number of cells in five high power fields (200×) was calculated. Each value denotes the average±SD of three independent trials.

Embodiment 4

Pathohistological and Immunohistochemical Analysis of Pathological Change in Rabbit Aortas Experimental Method The rabbits of both a test group (administered CTP30) and a control group (administered distilled water without the addition of CTP30) were sacrificed at three months and the aortas, hearts, and other organs were removed and fixed with formalin. The aortas were cut in cross-section into small segments (5 mm for each segment), embedded in paraffin, and employed in pathohistological and immunohistochemical analysis.

Pathohistological Analysis of the Aortas

Figure 14:
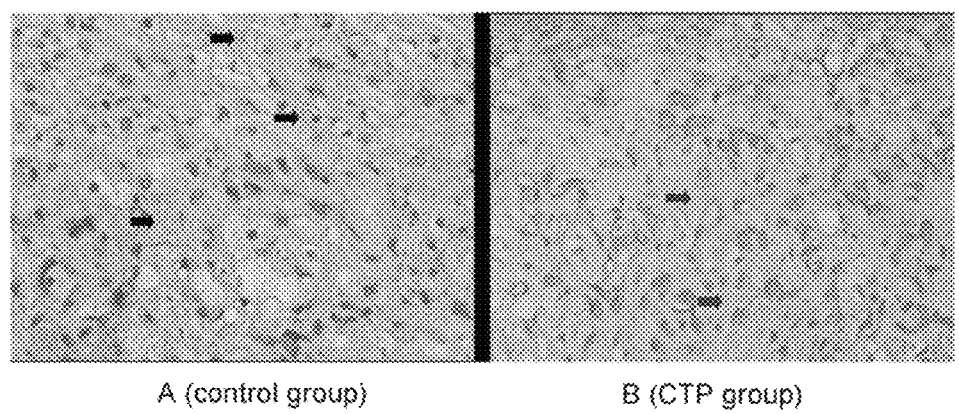
FIG. 14 shows the results of analysis of fibrosis of rabbit atherosclerosis loci (plaque) by Azan staining. Fig. A: The dark blue portions (black arrows) indicate worsen fibrotic regions with considerable collagen fiber. Fig. B: The light blue portions (blue arrows) indicate early fibrotic regions with sparse collagen fiber.

All the aorta specimens were stained with hemotoxylin and eosin (HE), Elastica-van Gieson (EVG), and Azan. The pathological changes were observed. The specimens presenting the most advanced pathological change to the aortic arch among the five rabbits of the test group and the five rabbits of the control group were stained with Azan to reveal the degree of fibrosis and compared. For each Azan-stained specimen, the area of the dark blue portions with considerable collagen deposition (advanced fibrotic regions, FIG. 14A) and the area of the light blue portions of little collagen deposition (early fibrotic regions, FIG. 14B) were analyzed and quantified with an Image-ProPlus 5.1. The quantification was conducted for five arbitrary visual fields at high magnification (400×) for both the test group and control group.

Results

The Effect of CTP30 on the Fibrosis of Atherosclerotic Loci (Plaque)

Figure 15:
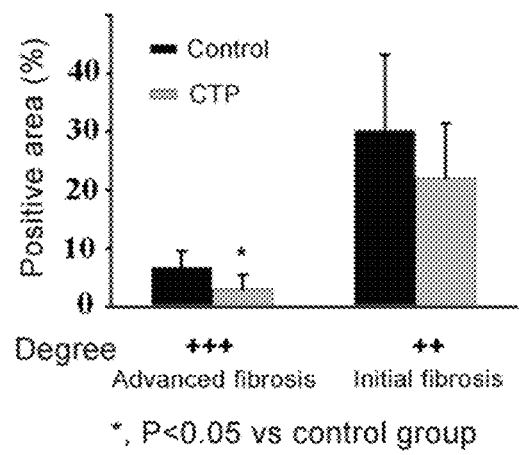
FIG. 15 shows the effect of CTP30 on fibrosis at rabbit atherosclerosis loci (plaque). It is a comparison of the area ratio (%) of dark blue portions (fibrosis) and light blue portions (sparse collagen) in the control group and CTP30 administered group (CTP).

As shown in FIG. 15, the CTP30-administered group (test group) exhibited a reduction in both advanced fibrotic regions and early fibrotic regions relative to the CTP30-nonadministered group (control group). This indicated that CTP30 inhibited excessive fibrosis.

No fibrosis was observed in other organs, including the lungs, liver, and kidneys (the results were not shown), and there were no negative effects due to side effects.

Immunohistochemical Analysis of the Aortas

The cell components (smooth muscle cells and macrophages) constituting pathological changes in the specimens presenting the most advanced pathological change in the aortic arch were immunohistochemically analyzed for the five rabbits of the test group and the five rabbits in the control group.

Figure 16:
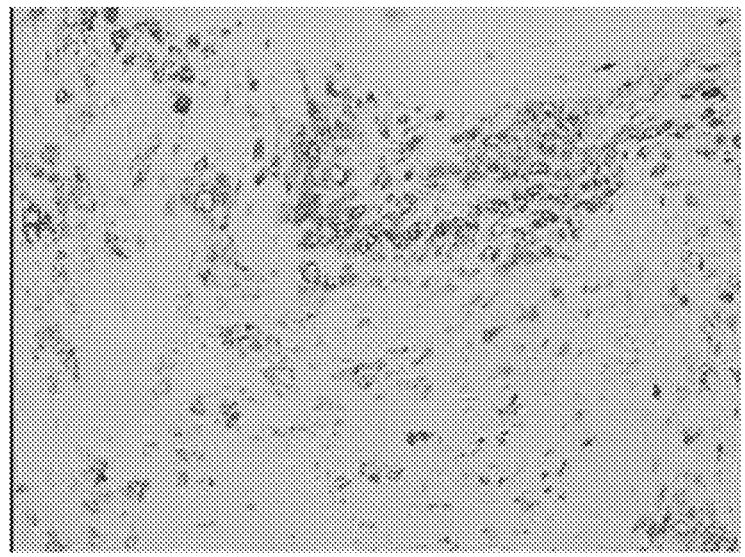
FIG. 16 shows the results of analysis of smooth muscle cells and macrophages in rabbit atherosclerosis loci (plaque) by immunohistology. A (RAM11): shows the localized presence of macrophages (brown cells) in plaque. B (HHF35): shows the localized presence of smooth muscle cells (brown cells) in plaque.
Figure 16:
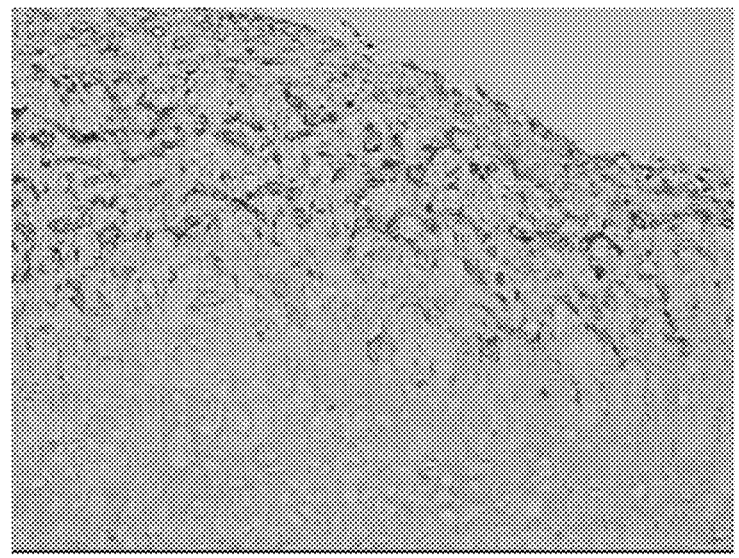

Paraffin sections were immunostained with anti-smooth muscle cell antibody (HHF35, Dako Japan, 1:50) and anti-macrophage antibody (RAM11, Dako Japan, 1:50), and quantitative analysis of each cellular composition was conducted with an Image-Pro Plus 5.1. The quantitation was conducted for five arbitrary visual fields at high magnification (200×) for both the test group and control group. FIG. 16 shows the RAM11-positive (brown) macrophages and HHF35-positive (brown) smooth muscle cells at atherosclerotic loci.

Results

The effect of CTP30 on the structure of smooth muscle cells and macrophages at the atherosclerotic loci (plaque)

Figure 17:
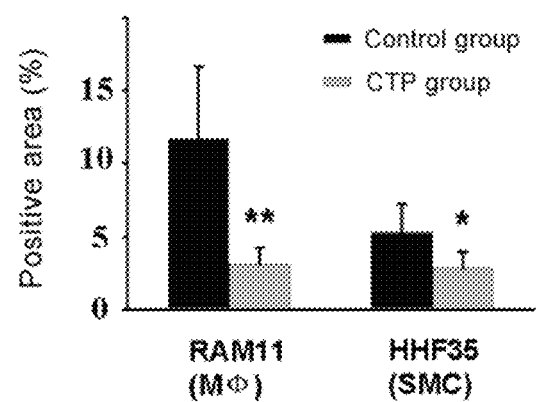
FIG. 17 shows the results of the effect of CTP30 on the composition of SMCs and macrophages at atherosclerotic loci (plaque).
Figure 18:
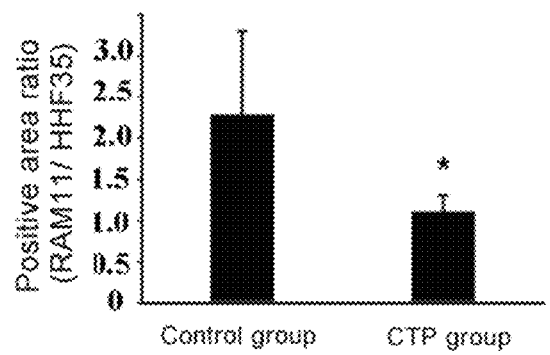
FIG. 18 shows a comparison of the ratio (of the areas) comprised of SMCs and macrophages in plaque in the CTP30-administered group and the control group.

FIG. 17 shows that more numerous cell components were present in plaque in the control group than in the CTP30-administered group, and that more macrophages (M) were present than smooth muscle cells (SMCs). This indicated that the principal cells in atherosclerotic loci (plaque) were macrophages. FIG. 18 shows that in the control group to which no CTP was added, more than twice as many macrophages were present as SMCs, and in the CTP30-administered group (CTP), macrophages and SMCs were present in about the same ratio.

The above results indicate that CTP30 has the effect of inhibiting both the infiltration and proliferation of macrophages in atherosclerotic loci (plaque).

Discussion

In in vivo experiments on familial hypercholesterolemic model rabbits, the group administered CTP30 for three months exhibited a significant decrease in total blood cholesterol and in the area of atherosclerotic pathologic change (plaque) on the surface of the aorta relative to the control group. Further, the deposition (fibrosis) of excess collagen fiber was inhibited. Still further, an immunohistochemical analysis of smooth muscle cells and macrophages, which are the main constituent cells of plaque, revealed that the CTP-administered group underwent a clear reduction in macrophages relative to the control group.

Macrophages produce and secrete various cytokines, growth factors, matrix metalloproteinases, and other protein-degrading enzymes in plaque, thereby promoting pathological change (Reference Document 4-1). Further, most of the lipids that seep into plaque are stockpiled in foam cells derived from macrophages. The collapse of foam cells causes cholesterol, cholesterol esters, and other lipids to accumulate outside cells. These extracellular lipids increase and protein degrading enzymes released by macrophages degrade collagen fiber and other extracellular matrix components. The plaque weakens and ruptures, forming blood clots accompanied by acute myocardial infarction and cerebral infarction. Thus, a reduction in macrophages has the effect of inhibiting the initiation, development, and rupture of plaque (Reverence Document 4-2).

The operative mechanism by which macrophages are reduced by CTP has not been clarified. However, it is said that the lowering of cholesterol causes a reduction in the gathering of macrophages in plaque and a reduction of protein degrading enzyme expression and activity (Reference Document 4-3), the cholesterol-reducing effect of CTP is thought to be a factor.

REFERENCE DOCUMENTS CITED IN EMBODIMENT 4

(4-1) Ross R: Atherosclerosis—An inflammatory disease. N Engl J Med, 1999, 340:115-126
(4-2) Libby P: Molecular bases of the acute coronary syndrome. Circulation, 1995, 91:2844-2850
(4-3) Masanori Aikawa: The stabilization of arteriosclerotic change by lipid-reducing treatments, *Experimental Medicine*, 2000, 18: 145-151.

Above-cited Reference Documents 4-1 to 4-3 are hereby incorporated by reference.

Comparative Example 1

The Effects of GELITA-SOL DA and GELITA-SOL LDA Aggl. on the Migration and Proliferation of Cultured Aortic Smooth Muscle Cells The effects of GELITA-SOL DA (derived from pig skin, average molecular weight about 5,000 to 7,000, made by DGF) and GELITA-SOL IDA Aggl. (derived from pig skin, average molecular weight about 3,000, made by DGF)—products equivalent to the hydrolysis products employed in the embodiments of Nonpatent Reference 12—on the migration and proliferation of cultured aortic smooth muscle cells were examined.

Experimental Method

The migration and proliferation testing of aortic smooth muscle cells (AoSMCs) was conducted by the same methods as for CTP30 (Embodiment 1) and CTP90 (Embodiment 3) set forth above.

Results

Figures 1, 19:
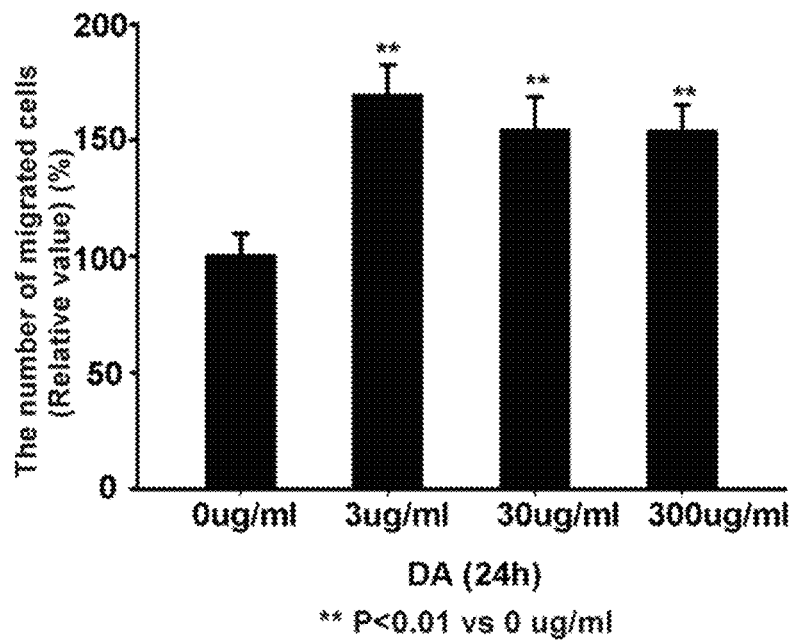
Figures 2, 19:
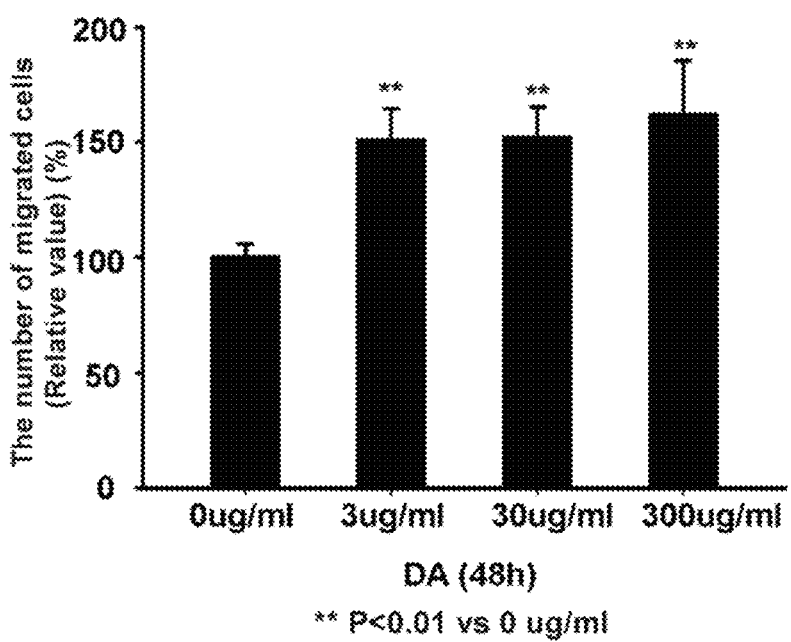
Figures 3, 19:
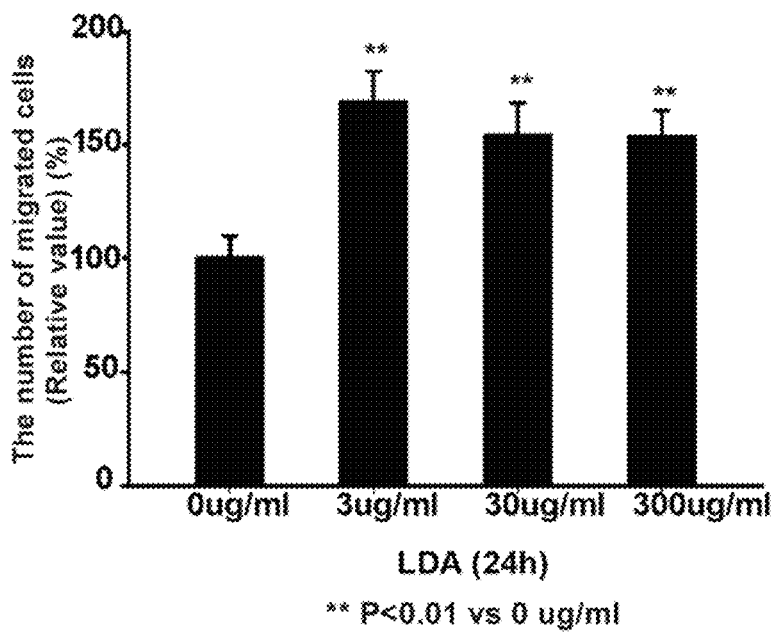
Figures 4, 19:
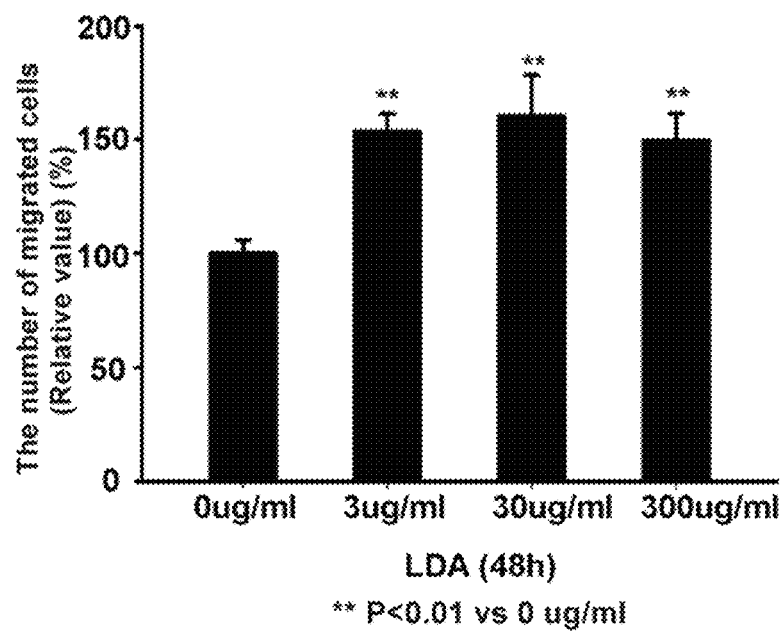

The Effects of GELITA-SOL DA (DA hereinafter) and GELITA-SOL IDA Aqql. (LDA Hereinafter) on the Migration of AoSMC DA and LDA were administered in three concentrations (3, 30, 300 μg/mL). After 24 hours and 48 hours, neither inhibited the migration of AoSMCs. Conversely, they promoted it. FIG. 19 shows the counts of migrated cells at 24 and 48 hours with the administration of DA and LDA, respectively, with the number of migrated AoSMCs in the control group as 100%. Each value indicates the relative average±SD (control group percentage) for four independent trials. As can be determined from FIG. 19, the groups administered DA and LDA exhibited significantly promoted migration relative to the control group (DA 0 μg/mL, LDA 0 μg/mL).

This indicates an effect the opposite of the migration-inhibiting effect of CTP indicated in Embodiments 1 and 3 (FIGS. 2 and 11). The fact that the migration of human aortic smooth muscle cells was enhanced was thought to increase the risk of the initiation and progression of atherosclerosis. Accordingly, DA and LDA, which are products equivalent to the collagen hydrolysis products described in Nonpatent Reference 12 were thought to increase the risk of the initiation and progression of atherosclerosis.

The Time-Course Effects of DA and LDA on SMC Proliferation

Figures 1, 20:
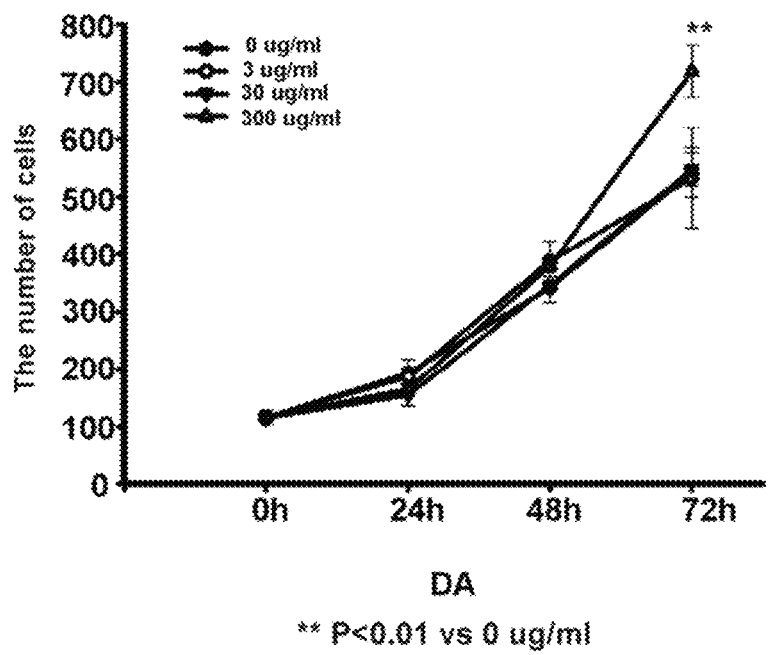
Figures 2, 20:
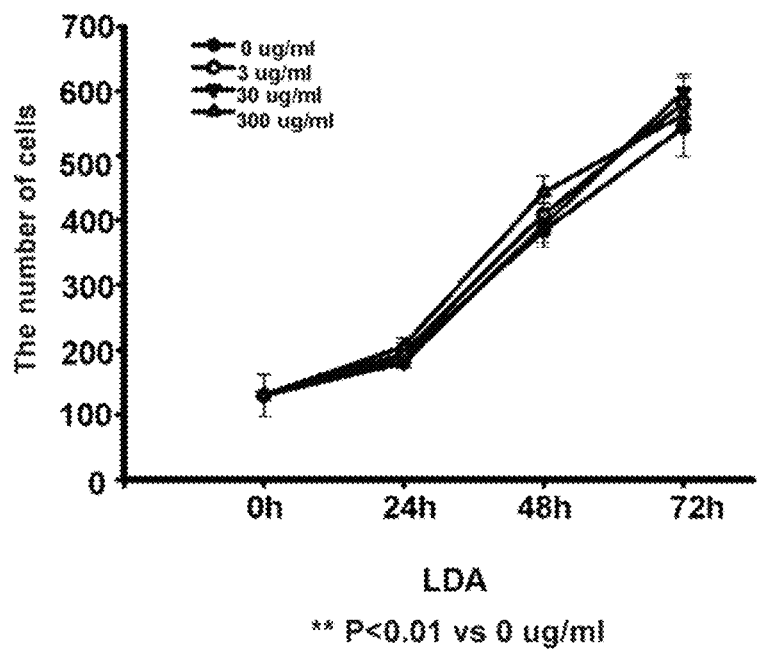

FIG. 20 shows the time-course change in the control group (0 μg/mL) and the effect of three concentrations (3, 30, 300 μg/mL) of DA and LDA on AoSMC proliferation. The various concentrations of DA and LDA were administered to AoSMC for the indicated periods. Subsequently, the total number of cells in five high power fields (200×) was calculated. Each value denotes the average±SD of three independent trials.

At 72 hours after the administration of 300 μg/mL of DA, a comparison to the control group indicated a promoting effect on AoSMC proliferation. The other DA-administered groups and LDA administered groups exhibited no clear promoting or inhibitory effect.

Compared to the effect of cell proliferation of CTP indicated in Embodiment 1 and 3 (FIGS. 6 and 13), none from among CTP 30 and 90 and DA and IDA exhibited a marked reduction with culture time. Thus, no cell toxicity was thought to be present. In addition, following the administration of 300 μg/mL of DA, significant AoSMC proliferation was exhibited. Thus, consideration based on the onset mechanism of atherosclerosis leads one to anticipate a poor effect. That is, consideration of DA, which is a product equivalent to the collagen hydrolysis product described in Nonpatent Reference 12, based on the onset mechanism of atherosclerosis leads one to anticipate a poor effect.

The Effects of DA and LDA on the PCNA-Positive Cell Ratio in AoSMCs

Figures 1, 21:
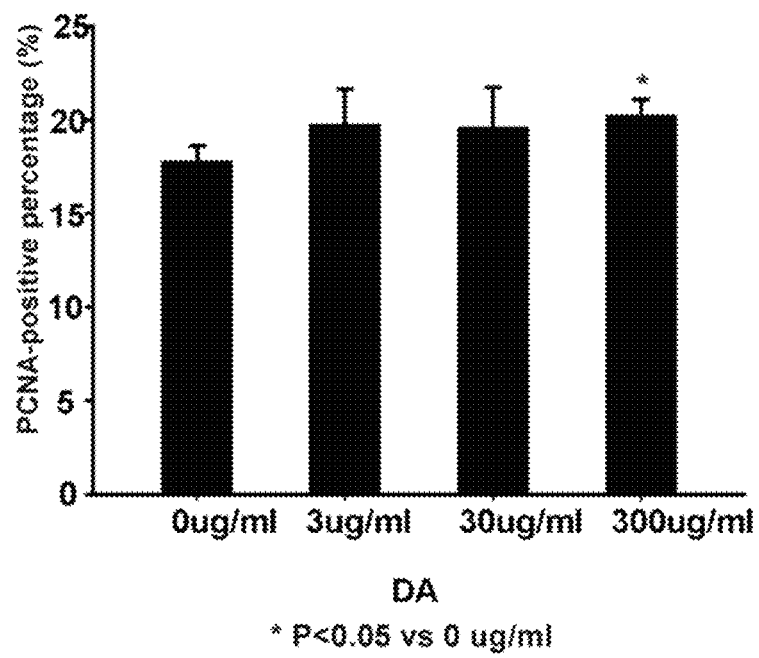
Figures 2, 21:
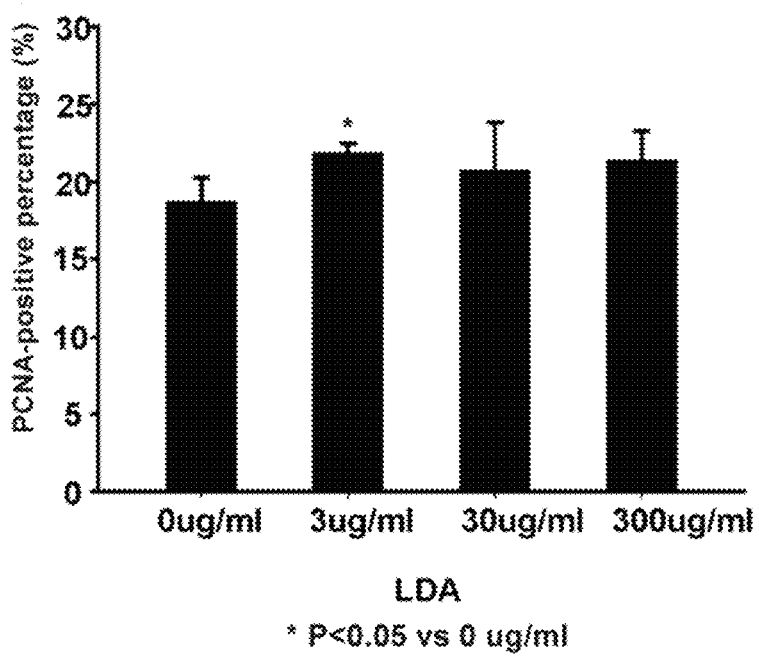

FIG. 21 shows the effect of the control group (0 μg/mL) and the effect of three concentrations (3, 30, 300 μg/mL) of DA and LDA on the PCNA-positive cell ratio in AoSMCs. The various concentrations of DA and LDA were administered to AoSMCs for 24 hours. Subsequently, as described in Embodiments 1 and 3 (FIGS. 5 and 12), the PCNA immunocytochemistry was implemented and the positive ratio was calculated in 10 high power fields (200×). Each value in FIG. 21 denotes the average±SD of three independent trials and indicates the ratio of PCNA-positive cells. The various concentrations of both DA and LDA all exhibited a tendency to increase the ratio of PCNA-positive cells relative to the control group.

A comparison of the ratio of PCNA-positive cells when cultured with the addition of CTP to that of the control group indicated that DA and LDA had the effect of increasing cells during the proliferation phase of AoSMCs.

The lively proliferation of AoSMCs presents the risk of promoting atherosclerosis and does not indicate a good effect for DA and LDA on atherosclerosis, strongly suggesting a negative effect (promotion of atherosclerosis).

Reference Examples

Figure 22:
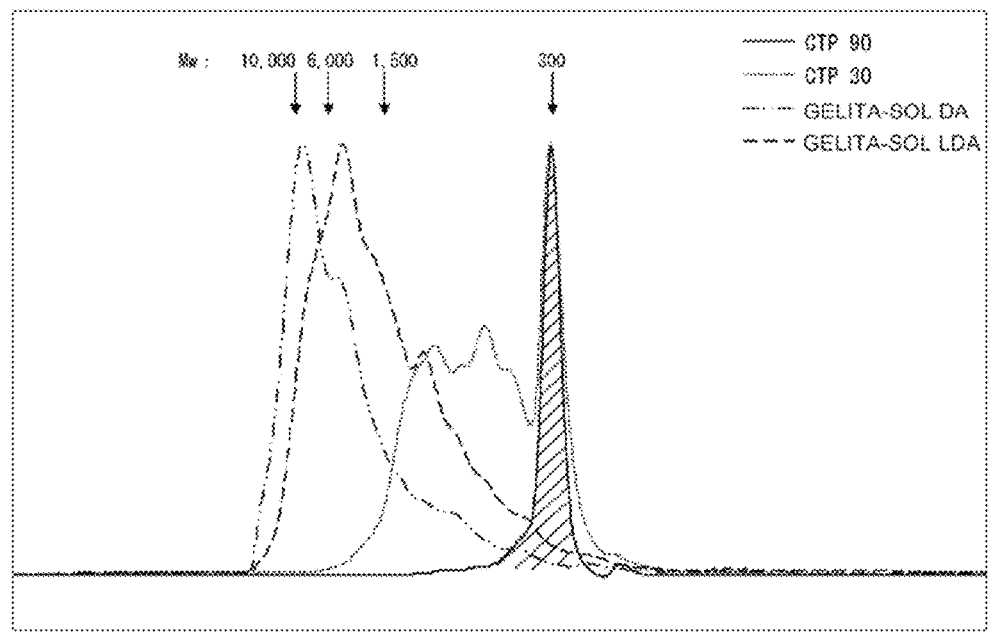
FIG. 22 shows HPLC chromatograms of the CP components (DA and LDA) of Gelita Corp. employed in the comparative examples, and of the CTP30 and 90 used in the embodiments.

FIG. 22 shows HPLC chromatograms of the CP components (DA and LDA) of Gelita that were employed in the above comparative example and CTP30 and 90 that were employed in the embodiments. The HPLC measurement conditions were as follows.

Column: Superdex Peptide 10/300 GL (GE Healthcare Japan, Ltd.)
Eluent: 10 mM Tris-HCl (pH 7.4), 150 mM NaCl, 5 mM $CaCl_2$
Flow rate: 1 mL/min
Analysis period: 30 min
Detection: UV (214 nm)

As set forth above, CTP30 has a collagen tripeptide Gly-X-Y content of 25 to 35 mass % and a Gly-X and X-Y content of about 10 mass %. The remainder is tetramer and higher hydrolysis products of amino acids of greater molecular weight than tripeptides. The tetramer and higher hydrolysis compounds of amino acids have a maximum molecular weight of about 6,000. CTP90 has a collagen tripeptide Gly-X-Y content of 85 to 100 mass %. The remainder is Gly-X and X-Y, and tetramer and higher hydrolysis products of amino acids of greater molecular weight than tripeptides.

By contrast, the main components of DA have molecular weights falling within a range of about 5,000 to 10,000, and the main components of LDA have molecular weights falling within a range of about 1,000 to 8,000. Both have extremely low collagen tripeptide Gly-X-Y contents. DA contains almost none of the peptides with molecular weights of 500 to 1,500 that are contained in greatest abundance after the main component in CTP30. In LDA, as well, the content of the peptides with molecular weights of 500 to 1,500 that are contained in greatest abundance after the main component in CTP30 is also low.

Based on the composition of these collagen peptides and the results of the above embodiments and comparative example, collagen hydrolysis products with main components with molecular weights ranging from about 5,000 to 10,000 and collagen hydrolysis products with main components with molecular weights ranging from about 1,000 to 8,000 have doubtful effects as drugs inhibiting the progression of atherosclerosis and preventive drugs. By contrast, the collagen hydrolysis product containing the collagen tripeptide Gly-X-Y (molecular weight about 300) of the present invention has been found to be effective as a drug inhibiting the progression of atherosclerosis and as a preventive drug.

INDUSTRIAL APPLICABILITY

The present invention is useful in the domain of manufacturing preventive drugs and drugs that inhibit the progression of atherosclerosis, blood cholesterol-lowering drugs, and functional foods and specific health foods that inhibit or prevent vascular aging and inflammation.

The invention claimed is:

1. A method of reducing the progression of atherosclerosis and lowering blood cholesterol, comprising administering to a patient affected with atherosclerosis and high blood cholesterol a hydrolysis product of a collagen containing collagen tripeptides Gly-X-Y, wherein Gly-X-Y denotes an amino acid sequence in which X and Y denote amino acid residues other than Gly, in an amount sufficient to reduce total blood cholesterol and at least one parameter selected from the group consisting of (i) migration of human aortic smooth muscle cells (AoSMC), (ii) plaque development and (iii) proliferating cell nuclear antigen (PCNA)-positive ratio in AoSMC in order to reduce the progression of atherosclerosis in the patient, wherein the collagen tripeptide hydrolysis product comprises Gly-Ala-Asp, Gly-Ala-Lys, Gly-Ala-Val, Gly-Pro-Gln, Gly-Pro-Met, Gly-Pro-Ile, Gly-Pro-Thr, Gly-Pro-Val, Gly-Ser-Hyp, Gly-Lys-Asp, Gly-Ala-Ala, Gly-Pro-Hyl, Gly-Leu-Hyp, Gly-Ala-Arg, Gly-Ala-Ser, Gly-Ala-Hyp, Gly-Gln-Glu, Gly-Glu-Gln, Gly-Pro-Ser, Gly-Pro-Lys, Gly-Pro-Ala, Gly-Pro-Pro, Gly-Pro-Arg and Gly-Pro-Hyp, and wherein the amount sufficient to reduce total blood cholesterol and the one parameter selected from the group consisting of: (i) migration of AoSMC; (ii) plaque development; and (iii) PCNA-positive ratio in AoSMC is from 10 to 1000 mg per kg of body weight.

2. The method of reducing the progression of atherosclerosis of claim 1, wherein the content of the collagen tripeptide Gly-X-Y in the hydrolysis product of a collagen ranges from 25 to 100 mass %.

3. The method of reducing the progression of atherosclerosis of claim 1, wherein the hydrolysis product of a collagen further comprises Gly-X or X-Y that is the degradation product of a collagen tripeptide Gly-X-Y.

4. The method of reducing the progression of atherosclerosis of claim 1, wherein the content of collagen tripeptides Gly-X-Y in the hydrolysis product of collagen ranges from 25 to 35 mass % and the hydrolysis product further comprises Gly-X and X-Y in amount of about 10 mass %.

5. The method of reducing the progression of atherosclerosis of claim 4, wherein the composition further comprises tetramers of the Gly-X-Y, Gly-X and X-Y peptides.

6. A method of lowering blood cholesterol, comprising administering to a patient in need thereof a hydrolysis product of a collagen containing collagen tripeptides Gly-X-Y, wherein Gly-X-Y denotes an amino acid sequence in which X and Y denote amino acid residues other than Gly, in an amount sufficient to reduce total blood cholesterol, wherein the collagen tripeptide hydrolysis product comprises Gly-Ala-Asp, Gly-Ala-Lys, Gly-Ala-Val, Gly-Pro-Gln, Gly-Pro-Met, Gly-Pro-Ile, Gly-Pro-Thr, Gly-Pro-Val, Gly-Ser-Hyp, Gly-Lys-Asp, Gly-Ala-Ala, Gly Pro Hyl, Gly-Leu-Hyp, Gly-Ala-Arg, Gly-Ala-Ser, Gly-Ala-Hyp, Gly-Gln-Glu, Gly-Glu-Gln, Gly-Pro-Ser, Gly-Pro-Lys, Gly-Pro-Ala, Gly-Pro-Pro, Gly-Pro-Arg and Gly-Pro-Hyp, and wherein the amount sufficient to reduce total blood cholesterol is from 10 to 1000 mg per kg of body weight.

7. The method of lowering blood cholesterol of claim 6, wherein the hydrolysis product of a collagen comprises 25 to 100 mass % of the collagen tripeptide Gly-X-Y.

8. The method of lowering blood cholesterol of claim 6, wherein the hydrolysis product of a collagen further comprises Gly-X or X-Y that is the degradation product of a collagen tripeptide Gly-X-Y.

* * * * *